United States Patent
Kosierkiewicz

(10) Patent No.: US 11,806,521 B1
(45) Date of Patent: Nov. 7, 2023

(54) SYSTEM AND METHOD FOR A DRY ELASTOMER ELECTRODE IN A WEARABLE GARMENT

(71) Applicant: Tomasz Andrzej Kosierkiewicz, Mount Vernon, IL (US)

(72) Inventor: Tomasz Andrzej Kosierkiewicz, Mount Vernon, IL (US)

( * ) Notice: Subject to any disclaimer, the term of this patent is extended or adjusted under 35 U.S.C. 154(b) by 335 days.

(21) Appl. No.: 16/820,545

(22) Filed: Mar. 16, 2020

Related U.S. Application Data

(60) Continuation-in-part of application No. 15/427,025, filed on Feb. 7, 2017, now Pat. No. 10,588,539, which
(Continued)

(51) Int. Cl.
| | |
|---|---|
| *A61N 1/04* | (2006.01) |
| *A61N 1/36* | (2006.01) |
| *A61B 5/00* | (2006.01) |
| *B29C 65/48* | (2006.01) |
| *B29C 65/00* | (2006.01) |
| *A61B 5/24* | (2021.01) |
| *A61N 1/378* | (2006.01) |
| *B29K 683/00* | (2006.01) |

(Continued)

(52) U.S. Cl.
CPC .......... *A61N 1/0488* (2013.01); *A61B 5/053* (2013.01); *A61B 5/24* (2021.01); *A61B 5/6832* (2013.01); *A61N 1/0456* (2013.01); *A61N 1/0484* (2013.01); *A61N 1/36021* (2013.01); *B29C 65/486* (2013.01); *B29C 65/4855* (2013.01); *B29C 66/45* (2013.01); *B29C 66/73141* (2013.01); *B32B 7/02* (2013.01); *B32B 7/12* (2013.01); *B32B 27/283* (2013.01); *B32B 37/10* (2013.01); *B32B 37/12* (2013.01); *A61B 2562/0209* (2013.01); *A61B 2562/04* (2013.01); *A61B 2562/125* (2013.01); *A61B 2562/164* (2013.01); *A61N 1/3785* (2013.01); *B29K 2505/14* (2013.01); *B29K 2683/00* (2013.01); *B29L 2031/752* (2013.01); *B29L 2031/753* (2013.01); *B32B 2255/10* (2013.01); *B32B 2305/30* (2013.01); *B32B 2307/202* (2013.01); *B32B 2383/00* (2013.01); *B32B 2535/00* (2013.01)

(58) Field of Classification Search
None
See application file for complete search history.

(56) References Cited

U.S. PATENT DOCUMENTS

| | | |
|---|---|---|
| 5,075,038 A | 12/1991 | Cole et al. |
| 5,263,481 A | 11/1993 | Axelgaard |

(Continued)

*Primary Examiner* — Catherine M Voorhees
*Assistant Examiner* — Elizabeth K So
(74) *Attorney, Agent, or Firm* — Jessica W. Smith; LOZA & LOZA, LLP

(57) ABSTRACT

A wearable garment includes a compression fabric with at least one electrode coupled to the compression fabric or sewn into seams of the wearable garment. The electrode includes a first layer comprising a metal integral conductive silicone rubber material configured to lay proximate to a wearer of the garment. The electrode may also include a second layer including a conducting metal sheet and a conductive lead coupled to the second layer. A non-conducting layer is configured to lay proximate to the compression fabric.

17 Claims, 18 Drawing Sheets

Related U.S. Application Data is a division of application No. 14/019,114, filed on Sep. 5, 2013, now Pat. No. 9,586,038, which is a continuation-in-part of application No. 13/020,392, filed on Feb. 3, 2011, now Pat. No. 8,569,935, which is a continuation-in-part of application No. 12/835,972, filed on Jul. 14, 2010, now abandoned, which is a continuation-in-part of application No. 12/559,061, filed on Sep. 14, 2009, now abandoned.

(60) Provisional application No. 61/819,574, filed on May 4, 2013, provisional application No. 61/788,575, filed on Mar. 15, 2013, provisional application No. 61/347,963, filed on May 25, 2010.

(51) Int. Cl.

| | | |
|---|---|---|
| *A61B 5/053* | (2021.01) | |
| *B32B 7/02* | (2019.01) | |
| *B32B 7/12* | (2006.01) | |
| *B32B 27/28* | (2006.01) | |
| *B32B 37/10* | (2006.01) | |
| *B32B 37/12* | (2006.01) | |
| *B29K 505/14* | (2006.01) | |
| *B29L 31/00* | (2006.01) | |

(56) References Cited

U.S. PATENT DOCUMENTS

| | | |
|---|---|---|
| 5,501,764 A | 3/1996 | Inselmann |
| 5,520,683 A | 5/1996 | Subramaniam |
| 6,156,236 A | 12/2000 | Hayashida et al. |
| 6,734,250 B2 | 5/2004 | Azechi et al. |
| 2005/0015134 A1 | 1/2005 | Carim |
| 2010/0000781 A1 | 1/2010 | Tanaka et al. |
| 2014/0113433 A1 | 4/2014 | Nguyen |
| 2015/0306373 A1* | 10/2015 | Bouton ............... G06F 3/015 607/148 |
| 2017/0100300 A1* | 4/2017 | Rapp ................. A61B 5/6828 |
| 2018/0003579 A1* | 1/2018 | Esposito ............... D04B 1/26 |

* cited by examiner

SYSTEM AND METHOD FOR A DRY ELASTOMER ELECTRODE IN A WEARABLE GARMENT

CROSS-REFERENCE TO RELATED APPLICATIONS

This present U.S. Utility Patent Application claims priority as a continuation-in-part application under 35 U.S.C. § 120 to U.S. patent application Ser. No. 15/427,025 entitled, "METHOD FOR A DRY ELASTOMER ELECTRODE," filed Feb. 7, 2017, issued as U.S. Pat. No. 10,588,539 on Mar. 17, 2020, which is incorporated by reference herein and made part of the present U.S. Utility Patent Application for all purposes, which:
- claims priority as a divisional application under 35 U.S.C. § 120 to U.S. patent application Ser. No. 14/019,114 entitled, "SYSTEM AND METHOD FOR A DRY ELASTOMER ELECTRODE," filed Sep. 5, 2013, now U.S. Pat. No. 9,586,038 Issued Mar. 7, 2017;
- claims priority to U.S. Provisional Application Ser. No. 61/788,575, entitled, "SYSTEM AND METHOD FOR A DRY ELASTOMER ELECTRODE," filed Mar. 15, 2013;
- claims priority to U.S. Provisional Application Ser. No. 61/819,574, entitled, "SYSTEM AND METHOD FOR A DRY ELASTOMER ELECTRODE," filed May 4, 2013;
- claims priority as a continuation-in-part application of U.S. application Ser. No. 13/020,392, entitled "PIEZOELECTRIC SHOE INSERT" filed Feb. 3, 2011, now U.S. Pat. No. 8,569,935 issued Oct. 29, 2013;
- claims priority as a continuation-in-part of U.S. application Ser. No. 12/835,972, filed Jul. 14, 2010, now abandoned;
- which is a continuation-in-part of application Ser. No. 12/559,061, filed Sep. 14, 2009, now abandoned, and
- claims benefit of U.S. Provisional Application Ser. No. 61/347,963, filed May 25, 2010;

all of which are incorporated by reference herein and made part of the present U.S. Utility Patent Application for all purposes.

FIELD

This application relates generally to electrodes, and in particular to a low impedance dry stimulation and recording electrode with at least one layer having an elastomeric surface.

BACKGROUND

In the medical field, electrodes are utilized to establish electrical contact with the skin of a patient, and are commonly used for the administration of electrical signals to the patient as well as for receiving electrical signals generated in the body of the patient.

Contact between the electrode and the skin of the patient is typically made through the use of conductive gels, pastes or creams. The conductive gels, pastes or creams are typically applied directly to the surface of the skin of the patient. As can be appreciated, the use of these conductive products can be problematic, as they may produce bridging artifacts, may cause the electrode displacement, i.e., the electrode may slide away from the desired position, or may even dry out rendering the electrode useless and any recording impossible (pertaining mostly to prolonged intraoperative monitoring). The conductive gels, pastes or creams are messy and often irritate the skin of the patient. Another disadvantage of the conductive gels, pastes and creams is that they leave a residue on the skin of the patient subsequent to the removal of the electrode therefrom, thereby requiring additional cleaning of the patient when finished, thus extending the preparation and testing time.

Accordingly, there is a need for systems and methods for providing a dry elastomer electrode that can be utilized in the medical industry without the need for applying conductive gels, pastes or creams to the patient. Dry biocompatible elastomer electrodes are durable, and re-usable. Can be incorporated into fabrics and clothing and can be worn for long periods of time. The rubbery surface of the electrode provides a smooth and uniform contact surface with the skin. Silicone rubber traps moisture (sweat) which helps to reduce the skin-to-electrode impedance, and thereby reduces electrode susceptibility to motion artifacts and noise. On the other hand, traditional wet gel electrodes will not work on the skin of a diaphoretic patient.

SUMMARY

In one aspect, a wearable garment comprises a plurality of electrodes incorporated into the garment, wherein at least one of the plurality of electrodes includes a first layer comprising a metal integral conductive silicone rubber material; a second layer comprising a non-conducting layer; and a conductive lead positioned intermediate the first layer and the second layer.

In another aspect, a wearable garment comprises a compression fabric and a plurality of electrodes coupled to the compression fabric. At least one of the plurality of electrodes includes a first layer comprising a metal integral conductive silicone rubber material; a second layer including a conducting metal sheet; a conductive lead coupled to the second layer; and a non-conducting layer configured to lay proximate to the compression fabric.

In another aspect, a device includes a wearable garment including compression fabric; at least one electrode coupled to the compression fabric and a wireless transceiver coupled to the at least one electrode. The at least one electrode includes a first layer comprising a metal integral conductive silicone rubber material; a second layer including a conducting metal sheet; a conductive lead coupled to the second layer; and a non-conducting layer configured to lay proximate to the compression fabric.

In one or more of the above aspects, the first layer is configured for positioning most proximate to a wearer of the wearable garment.

In one or more of the above aspects, at least one of the plurality of electrodes further comprises a cover film, wherein the cover film is configured to protect the at least one of the plurality of electrodes from exposure.

In one or more of the above aspects, the at least one of the plurality of electrodes further comprises a water-resistant material, wherein the water-resistant material is configured to protect the at least one of the plurality of electrodes from moisture.

In one or more of the above aspects, the conductive lead is configured for connection to an electro-stimulation device for conducting an electrical stimulation signal to the at least one of the plurality of electrodes.

In one or more of the above aspects, the conductive lead is configured for connection to a wireless transceiver for transmission of physiological signals detected by the at least one of the plurality of electrodes to a monitoring device.

In one or more of the above aspects, the at least one of the plurality of electrodes further comprises an adhesive layer proximate to the wearable garment, wherein the adhesive layer couples the at least one of the plurality of electrodes to a fabric of the wearable garment.

In one or more of the above aspects, the at least one of the plurality of electrodes is sewn into a stitch seam of the wearable garment.

DETAILED DESCRIPTION

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from FIGs and descriptions thereof presented herein in order not to obscure the aspects of the disclosure.

Embodiment—Dry Elastomer Electrode

Figure 1A:
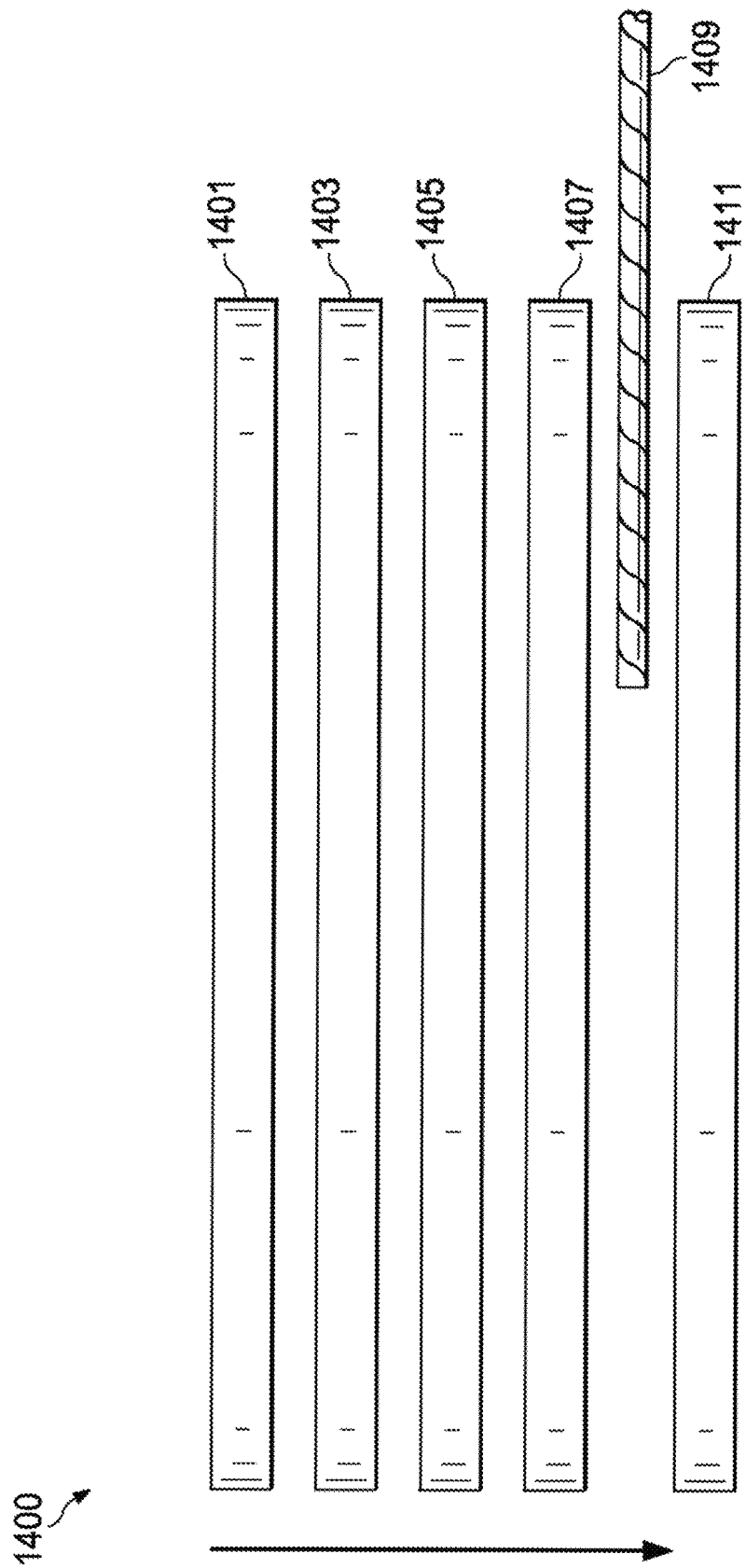
FIG. 1A is an exploded side view of an embodiment of a dry elastomer electrode.
Figure 1B:
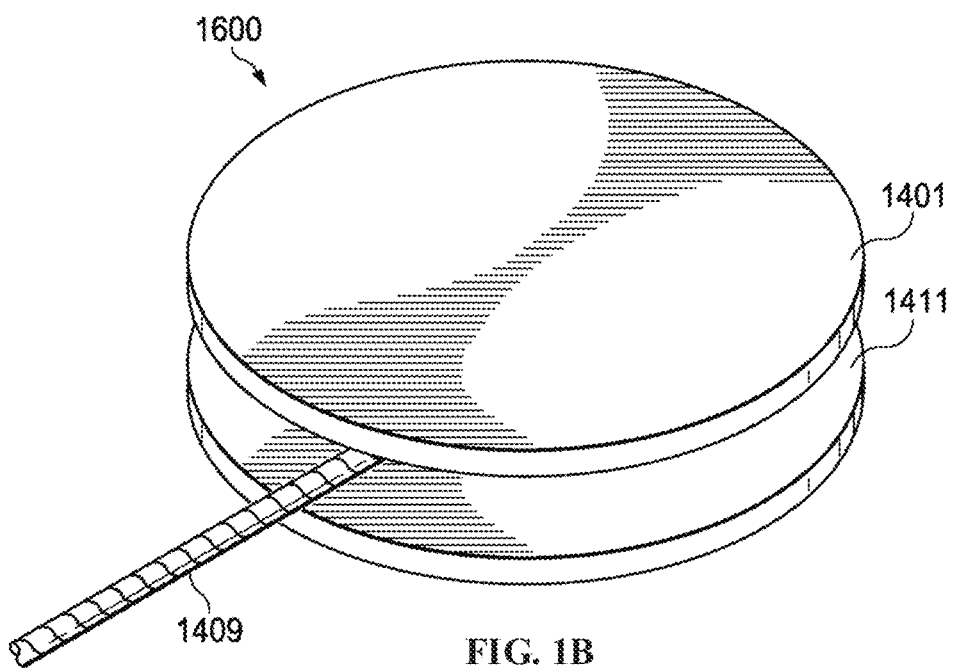
FIG. 1B is an exploded top perspective view of another embodiment of a dry elastomer electrode.
Figure 1C:
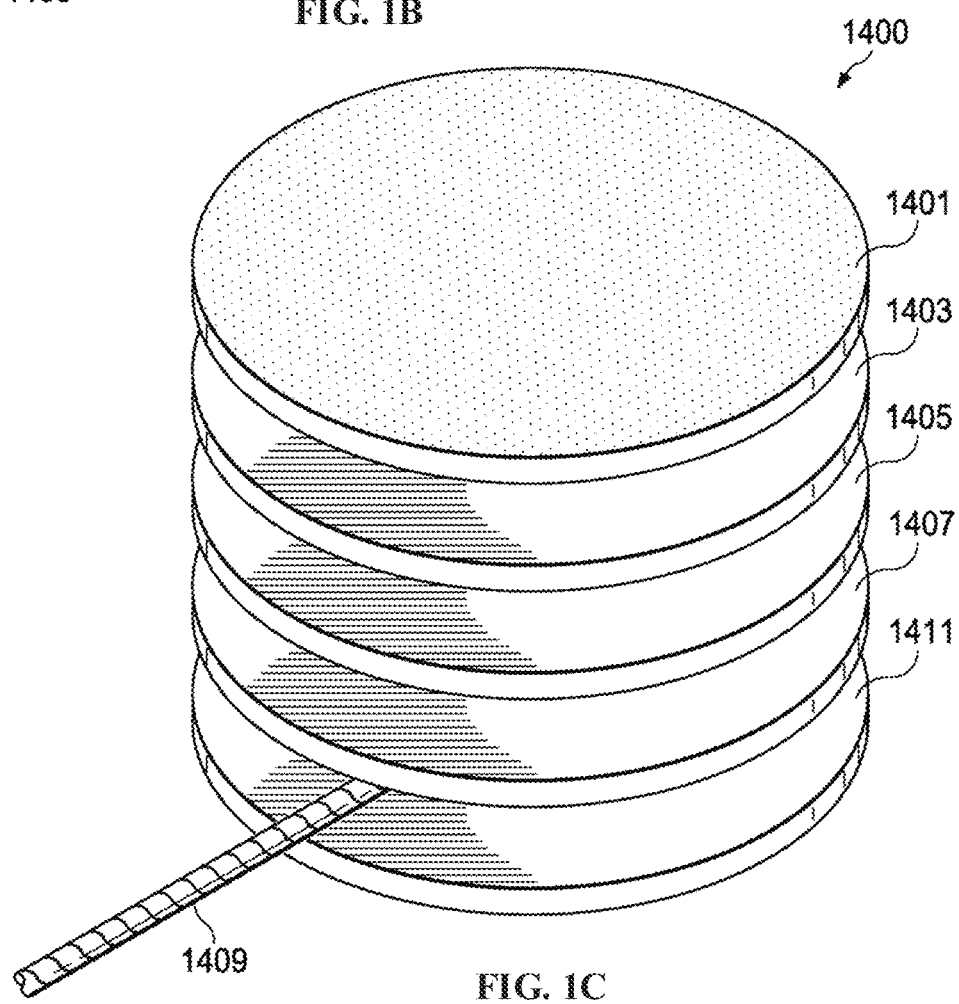
FIG. 1C is an exploded top perspective view of an embodiment of a dry elastomer electrode as similarly shown in FIG. 1A.
Figure 2:
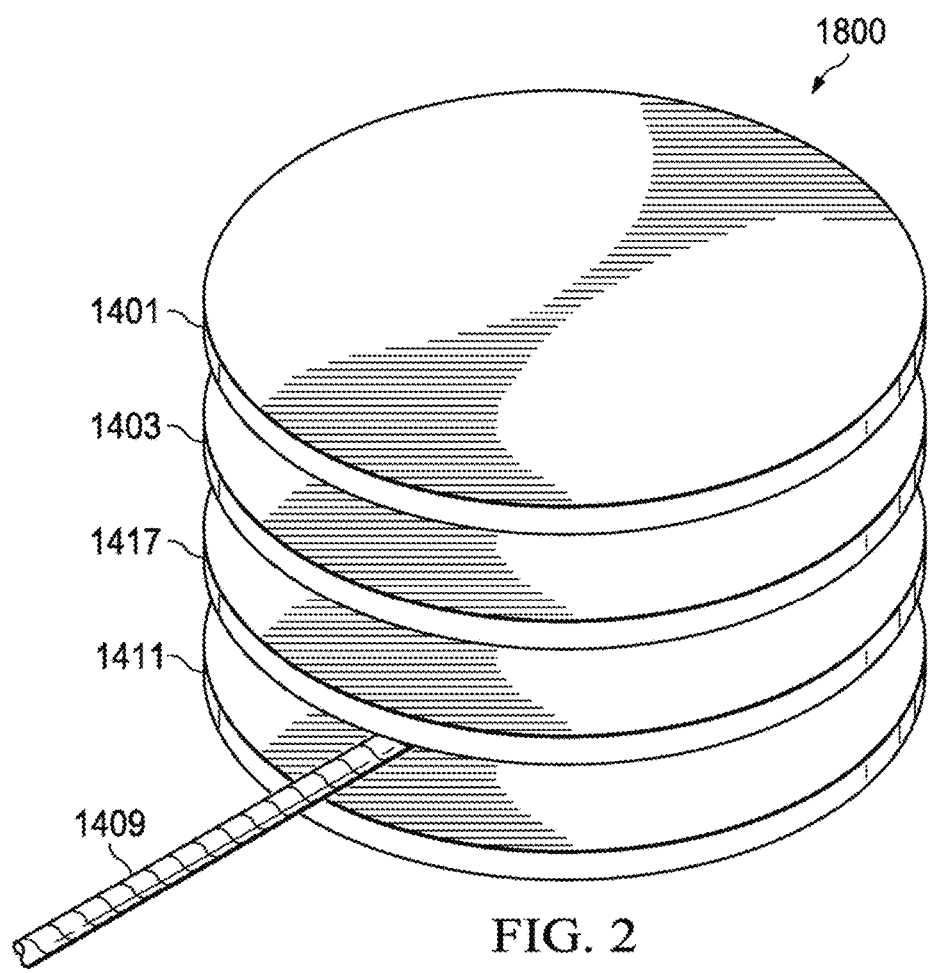
FIG. 2 is an exploded top perspective view of another embodiment of a dry elastomer electrode.

FIGS. 1A-C and FIG. 2 illustrate embodiments of a dry elastomer electrode. FIG. 1A is an exploded side view of an embodiment of a dry elastomer electrode 1400; FIG. 1B is an exploded top perspective view of another embodiment of the dry elastomer electrode 1600; and FIG. 1C is an exploded top perspective view of the embodiment of the dry elastomer electrode 1400, as similarly shown in FIG. 1A. FIG. 2 is an exploded top perspective view of another embodiment of a dry elastomer electrode 1800.

The electrodes 1400 (FIG. 1A and 1C), 1600 (FIG. 1B), and 1800 (FIG. 2) may be a transcutaneous medical electrode for stimulating nerves and/or muscles by generating electricity that could be used in different parts of the body. The electrodes 1400, 1600, and 1800 may be employed for other uses as well. For example, the electrodes 1400, 1600, 1800 may be used to detect a body's natural electric signals, e.g. for heart and respiration monitoring, electrocardiograms, pregnancy monitoring, infant monitoring, etc.

In an embodiment, the electrodes 1400, 1600, and 1800 include a substantially dry body comfortable, biocompatible, electrically conductive interfacing layer of a metal-integral conductive silicone rubber sheet. The dry elastomer electrodes 1400, 1600, and 1800 are employed for similar uses as adhesive electrodes or gel electrodes or where such electrodes may not be appropriate or desirable. For example, the electrodes 1400, 1600, and 1800 may replace an adhesive electrode, e.g. where allergic reaction may be possible.

FIGS. 1A and 1C illustrate an embodiment of the electrode 1400 which includes at least an upper/first sheet 1401 of metal integral conductive silicone rubber (or elastomer) which, by way of example and not limitation, may be a gold, silver, silver plated copper, graphite or other conductive metal plated material filled silicone. The silicone includes a silicon-containing synthetic polymer silicone or other material including silicone, such as silicone elastomers, silicone rubber, etc. Electrode 1400 further includes a second layer 1403 which may be a conductive adhesive gel layer to adhere to the first sheet 1401, a third sheet 1405 of a conductive carbon film to adhere to the second layer 1403, and a fourth sheet 1407 which may be a conductive metal sheet and the metal may be silver or other appropriate metals. An electrical lead 1409 is positioned and secured between the fourth sheet 1407 and the fifth sheet 1411. In one embodiment, the electrical lead 1409 facilitates the delivery of energy to the electrode 1400 from a power source (not shown) for electrical stimulation. In another embodiment, the lead 1409 may conduct detected electric signals of the body for heart monitoring, respiration monitoring, electrocardiograms or other types of monitoring. Fifth sheet 1411 may be a dielectric/non-conducting flexible backing sheet.

FIG. 1B illustrates another embodiment of the electrode 1600 which includes two layers 1401 and 1411. Electrode 1600 includes an upper/first sheet 1401 of metal integral conductive silicone rubber (or elastomer) which, by way of example and not limitation, may be a gold, silver, silver plated copper, graphite, or other conductive metal plated material filled silicon. Electrode 1600 further includes an electrical lead 1409 which is positioned and secured between the first sheet 1401 and the bottom sheet 1411. The electrical lead 1409 facilitates the delivery of energy to the electrode 1600 from a power/recording source (not shown). The bottom sheet 1411 may be a dielectric/non-conducting flexible backing sheet.

FIG. 2 illustrates another embodiment of the electrode 1800 which includes, e.g., four layers 1401, 1403, 1417 and 1411. The first or top layer 1401 is the interfacing layer and is a silver filled silicone rubber (or elastomer) skin interface. The second layer 1403 is a conductive adhesive layer that is positioned in-between first layer 1401 and third layer 1417. The third layer 1417 is an Ag/AgCl film and is positioned between second layer 1403 and fourth layer 1411. The fourth layer 1411 is a dielectric backing layer and is positioned below third layer 1417. An electrical lead 1409 is positioned and secured between the third layer 1417 and the fourth layer 1411. The electrical lead 1409 facilitates the delivery of energy to the electrode 1800 from a power/recording source (not shown) or conducting detected signals to a monitor.

Though the interfacing or upper layer is described as including the metal integral conductive silicone rubber (or elastomer), other layers may also include the elastomer covering, e.g. conductive inks, or other materials which may facilitate the prevention of corrosion. In addition, one or more other interfacing or upper layers may be added on top of the metal integral conductive silicone rubber (or elastomer) for interfacing with the skin. In another embodiment a plurality of metal integral conductive silicone rubber (or elastomer) layers may be used. The elastomer is preferably a conductive material with low volume resistivity, such as silicone rubber.

In an embodiment, a dry and flexible electrode is prepared by stacking the desired layers as described herein and pressing them. For the interfacing or top layer 1401, an electrically conductive silicone elastomer containing silver fillers is utilized. Then a pressure is applied to the electrode. The amount of pressure applied to the electrode layers depends upon the desired operating parameters for the electrode for a particular user.

Figure 11:
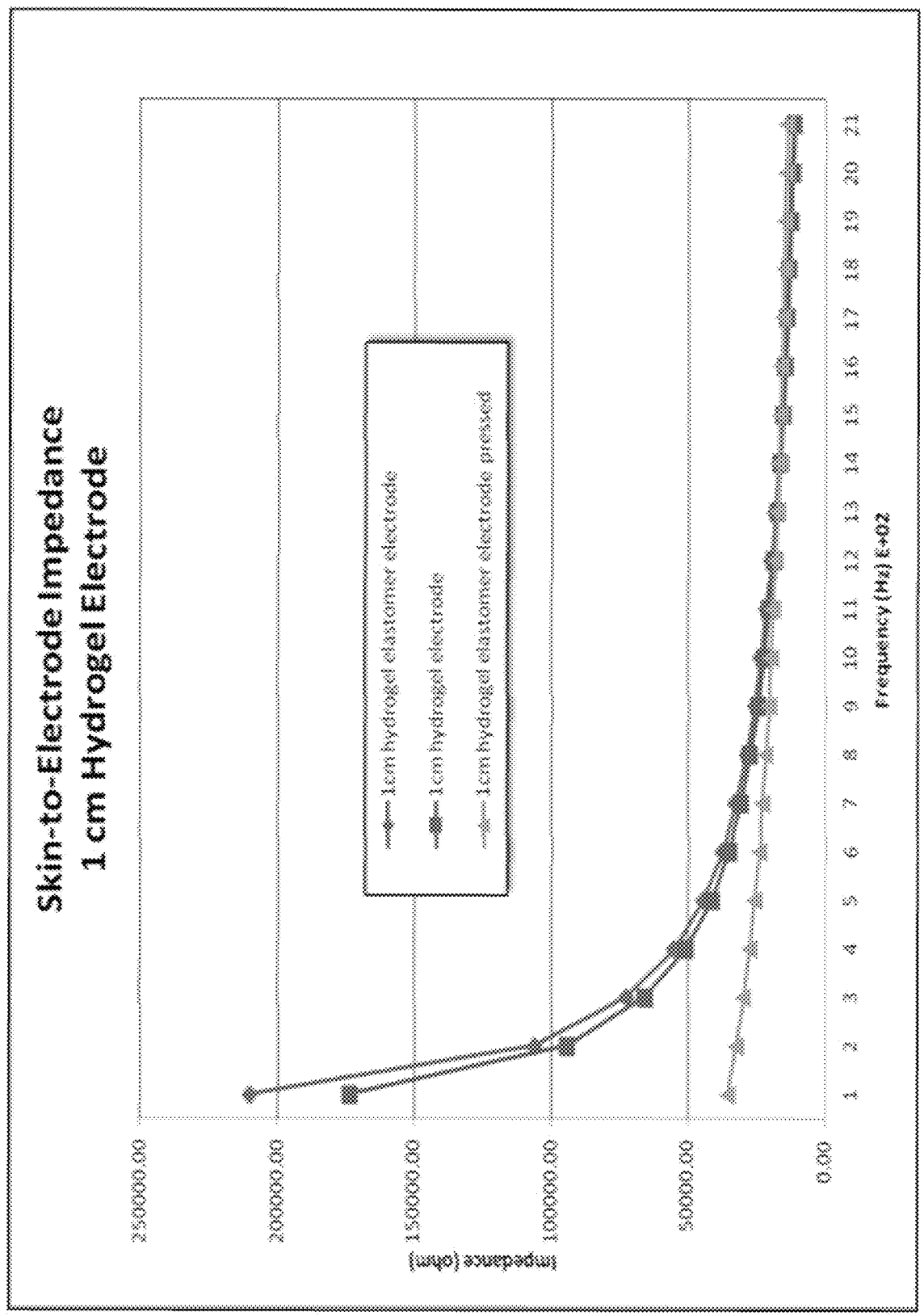
FIG. 11 illustrates a graph of skin to electrode impedance for an embodiment of a Hydrogel Electrode.
Figure 12:
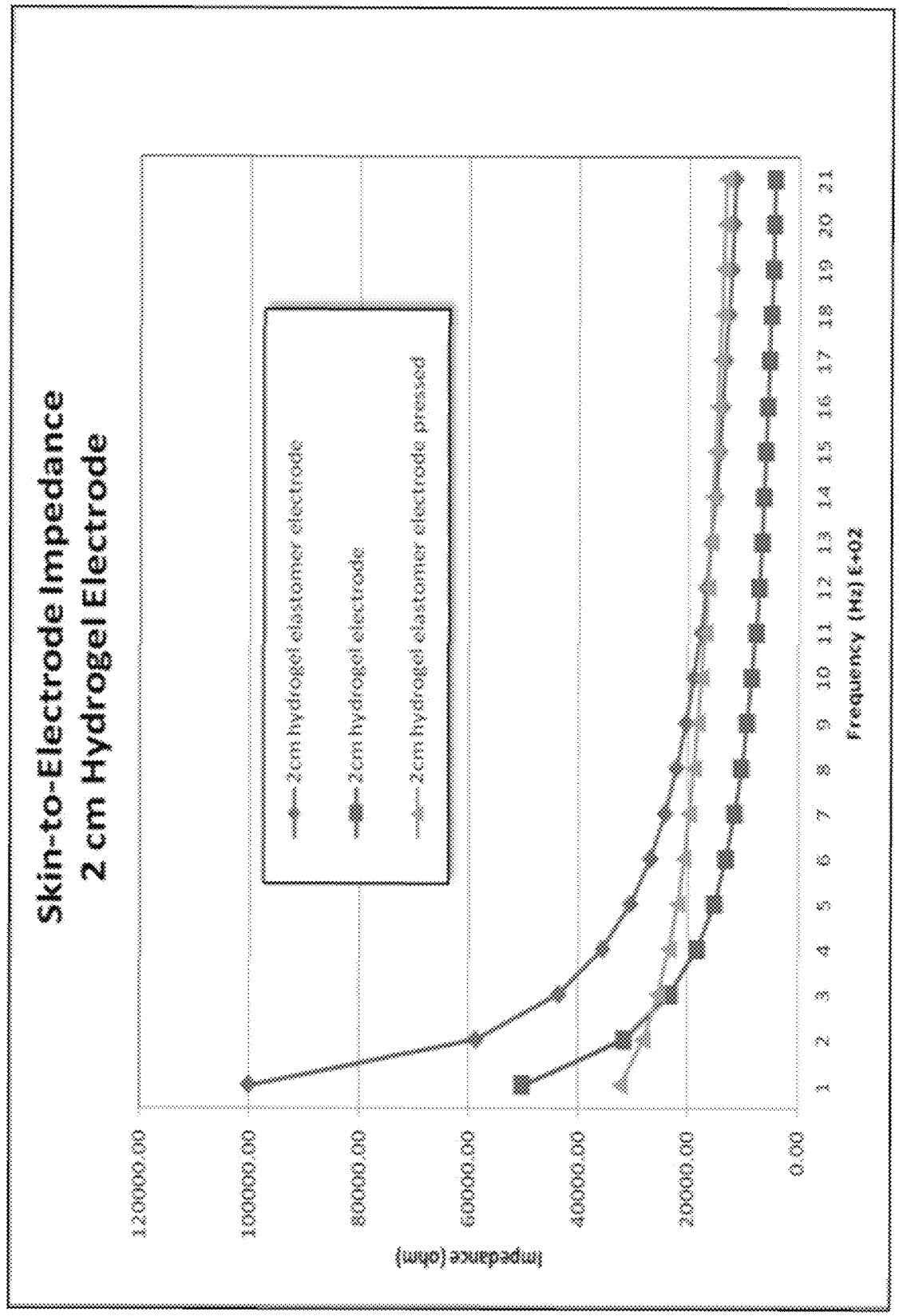
FIG. 12 illustrates a graph of skin to electrode impedance for another embodiment of a Hydrogel Electrode.
Figure 13:
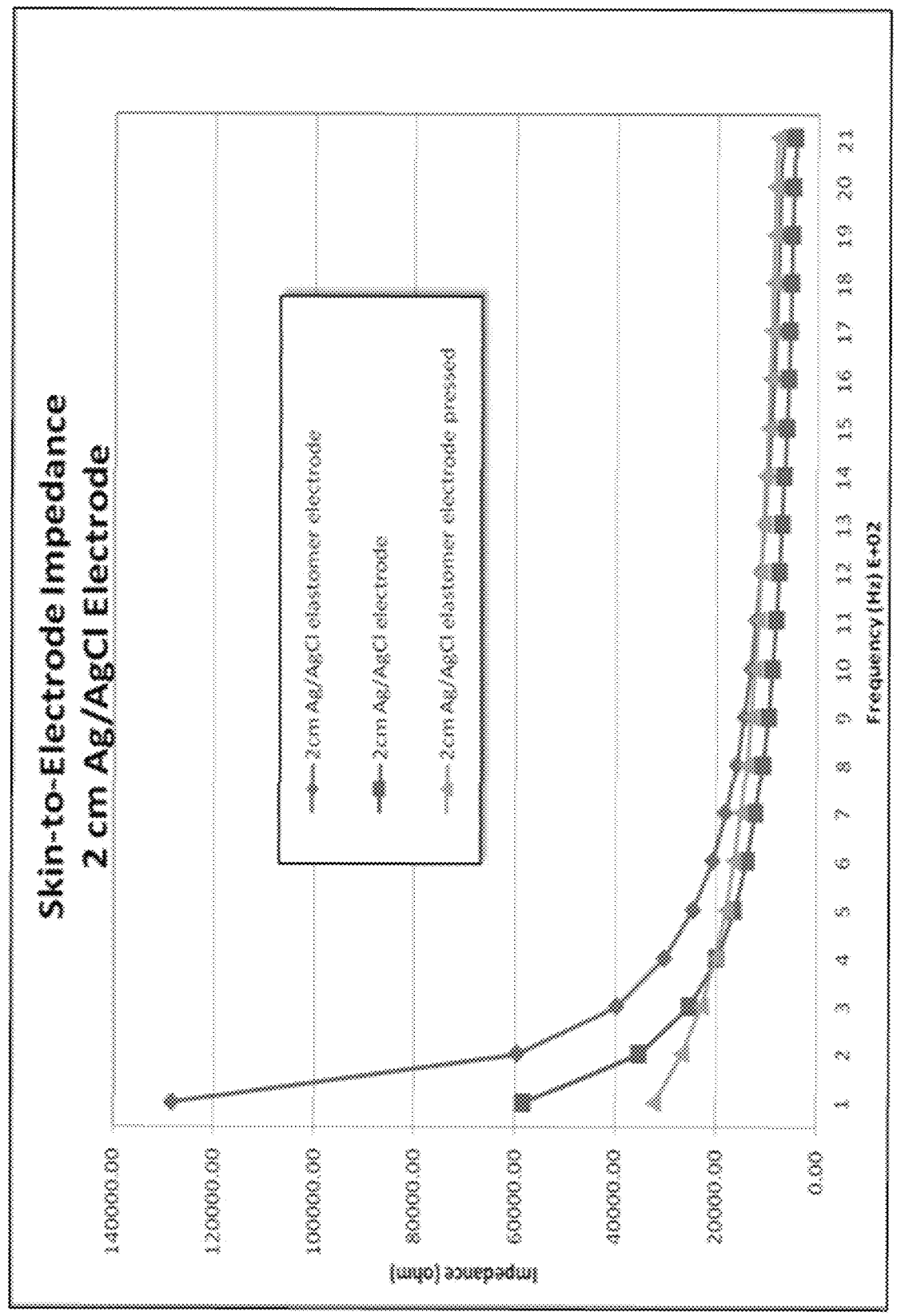
FIG. 13 illustrates a graph of skin to electrode impedance for an embodiment of an Ag/AgCl Electrode.
Figure 14:
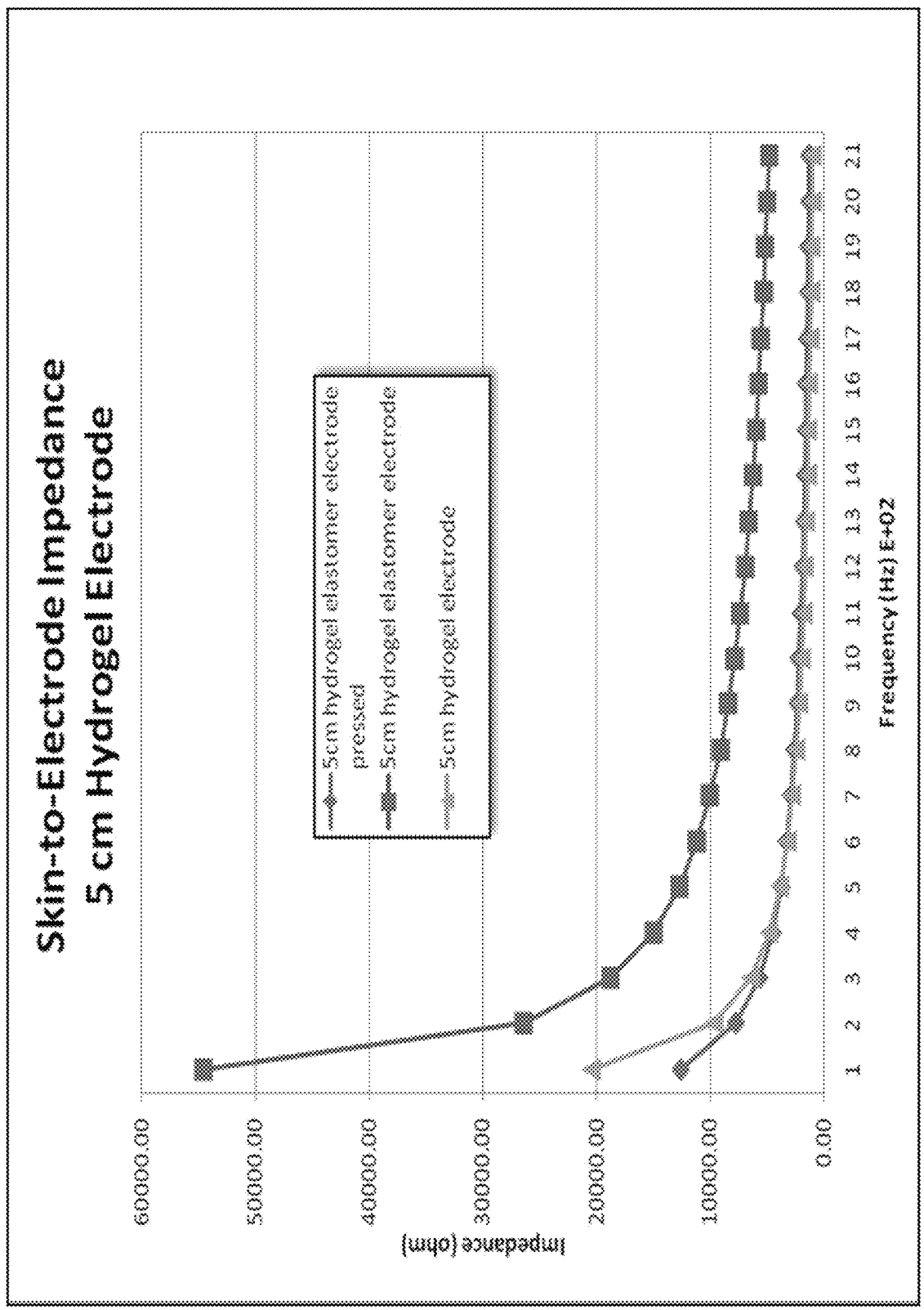
FIG. 14 illustrates a graph of skin to electrode impedance of another embodiment of a Hydrogel Electrode.

FIG. 11 illustrates a graph of skin to electrode impedance for an embodiment of a Hydrogel Electrode. FIG. 12 illustrates a graph of skin to electrode impedance for another embodiment of a Hydrogel Electrode. FIG. 13 illustrates a graph of skin to electrode impedance for an embodiment of an Ag/AgCl Electrode. FIG. 14 illustrates a graph of skin to electrode impedance of another embodiment of a Hydrogel Electrode. For example, in an embodiment, the pressure was approximately 429 PSI for a 5 cm (diameter) electrode and as high as approximately 2684 PSI for a 2 cm electrode and at approximately 11914 PSI for a 1 cm electrode though other pressures may facilitate optimal operation as well, as evidenced by the reduced electrode-skin impedance values. In an embodiment, lower electrode-skin impedance values were found as shown in FIGS. 11-14. FIGS. 11-14 illustrate how compression after laminating changes impedance of elastomer electrodes.

As seen in FIGS. 11-14, different values of impedance are observed, with pressure applied to an electrode, at different frequency ranges. In an embodiment, the pressure applied to an electrode is adjusted during manufacture to try to achieve a certain impedance for a desired frequency range. For example, as shown in FIG. 14, a 5 cm elastomer-hydrogel electrode with pressure applied has a lower impedance than similar hydrogel electrode, only at lower frequencies, and a much lower impedance than elastomer-hydrogel electrode that has been laminated but not pressed, across the entire frequency range. Similarly, as shown in FIG. 11, for a 1 cm elastomer-hydrogel electrode operating at a lower frequency range, more pressure may be applied during manufacture to the elastomer-hydrogel electrode to obtain a lower impedance value for that frequency range while less pressure is applied to a 1 cm elastomer-hydrogel electrode that is operating in a higher frequency range. Thus, pressure applied during manufacturing of an electrode is adjusted to attempt to optimize performance of the electrode at a required or desired frequency value.

In an embodiment, to mitigate the "edge effect" and to provide even current density distribution across the electrode, a given electrode is pressed concentrically, where increasingly higher force is applied from the periphery toward the center of the electrode, and thus creating a "segmented impedance" electrode or a varying impedance electrode with the higher impedance at the periphery of the electrode and the lowest resistance in the center of the electrode. For example with an electrode having at least 2.5 cm radius, the following could be utilized to create a "segmented impedance" electrode:

i. 2.5 cm radius is pressed with 500 PSI, then
  ii. 2.0 cm radius is pressed with 2000 PSI, then
  iii. 1.5 cm radius is pressed with 4000 PSI, then
  iv. 1.0 cm radius is pressed with 8000 PSI, then
  v. 0.5 cm radius is pressed with 12000 PSI.

Other radii and/or pressures applied to the electrode may be implemented in addition to or alternatively to those shown above. In an embodiment, the electrode has the physical structure of the electrode described herein. In another embodiment, the concentrically applied pressure may be used with an electrode having similar or other physical structures and shapes as well.

Although illustrated hereinabove in the various embodiments as circular shaped electrodes, it is contemplated that the claims are not limited to circular shaped electrodes. The electrodes of the claims could be of virtually any shape and size with the applied pressure varying from the outer most perimeter to the middle portions so as to provide a selected performance for a particular user.

FIGS. 3-10 illustrate various embodiments of form factors for use of the multilayered dry elastomer electrode as described hereinabove. Although FIGS. 3-10 are illustrated with a single embodiment of the electrode, it is contemplated that any of the electrode embodiments described herein could be utilized and be within the scope of the claims. It is further contemplated to be within the scope of the claims that other form factors and embodiments may also employ the multilayered dry elastomer electrode.

Figure 3:
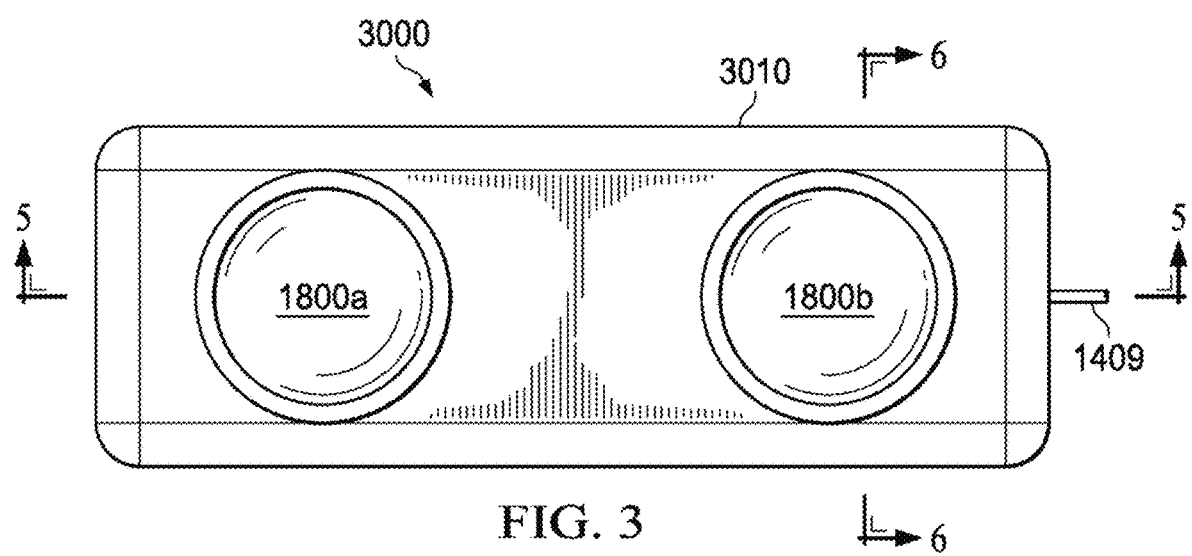
FIG. 3 is a top view of an embodiment of a dry elastomer electrode in a bar electrode.
Figure 4:
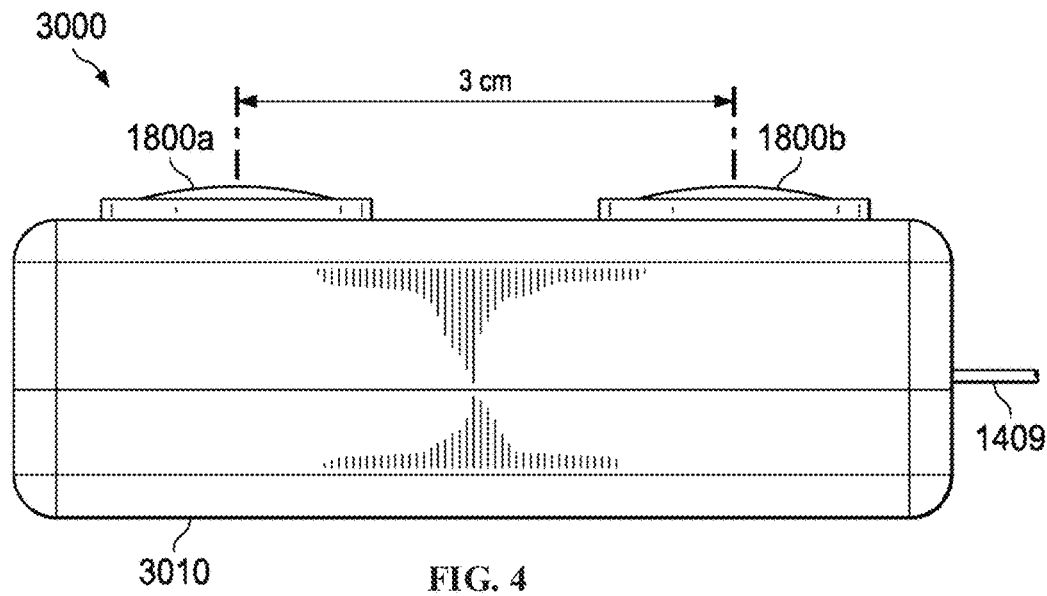
FIG. 4 is a side view of an embodiment of a dry elastomer electrode in a bar electrode as similarly shown in FIG. 3.
Figure 5A:
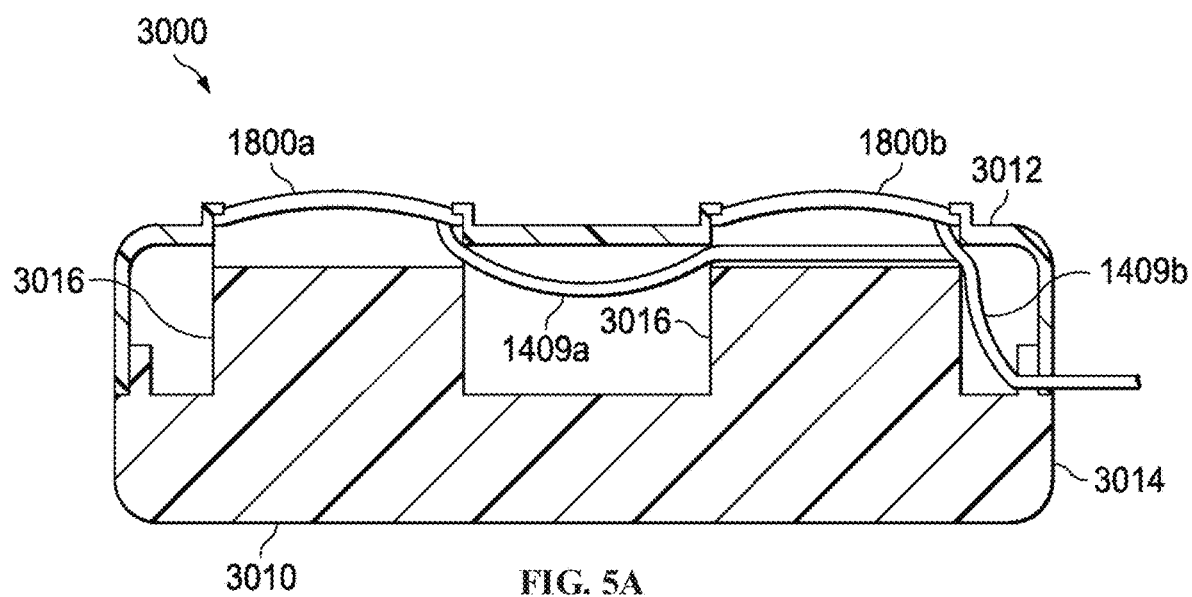
FIG. 5A is a cross-sectional side view of an embodiment of the bar electrode taken along line 5-5 of FIG. 3.
Figure 5B:
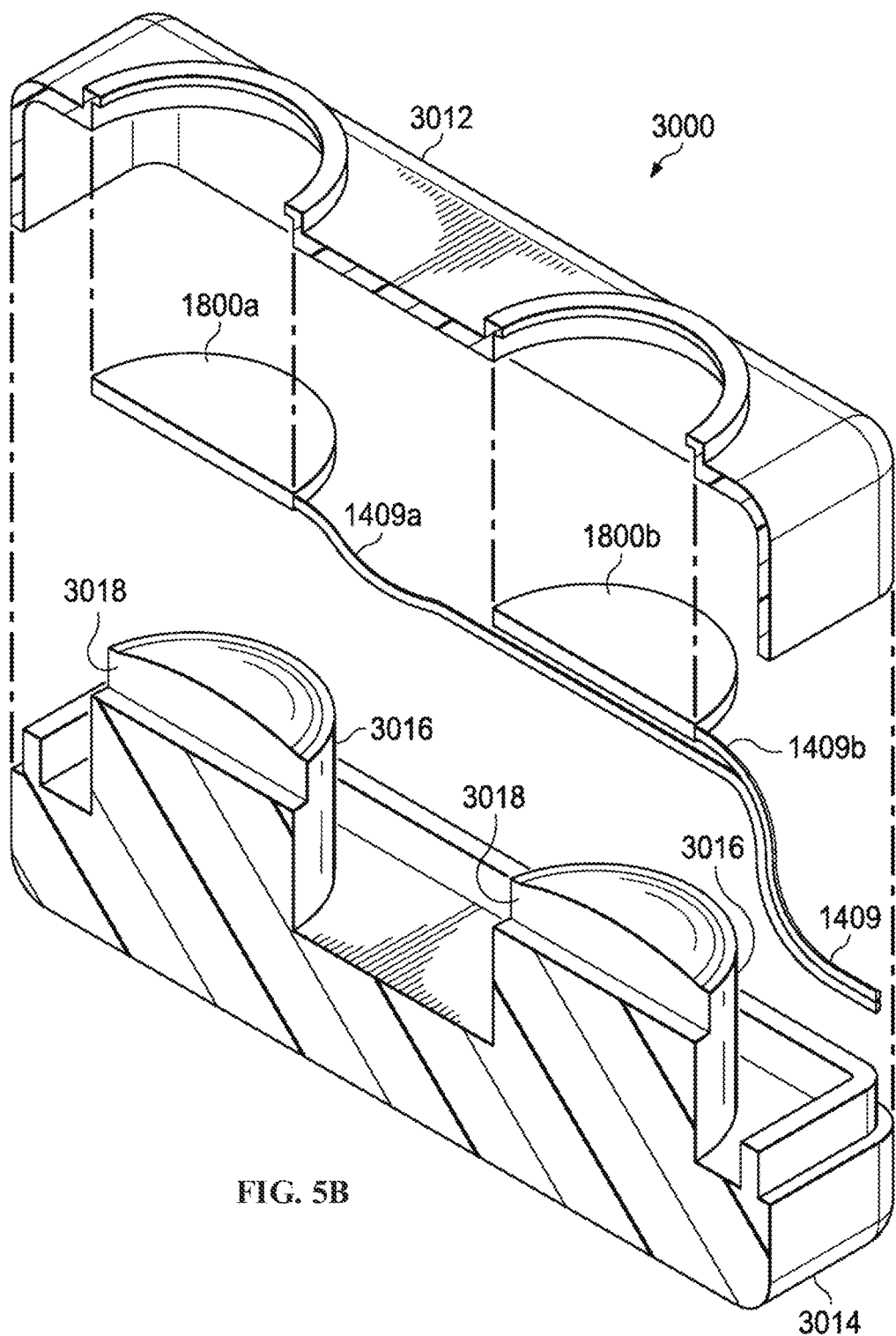
FIG. 5B is an exploded perspective view of an embodiment of the cross-sectional view of the bar electrode shown in FIG. 5A.
Figure 5C:
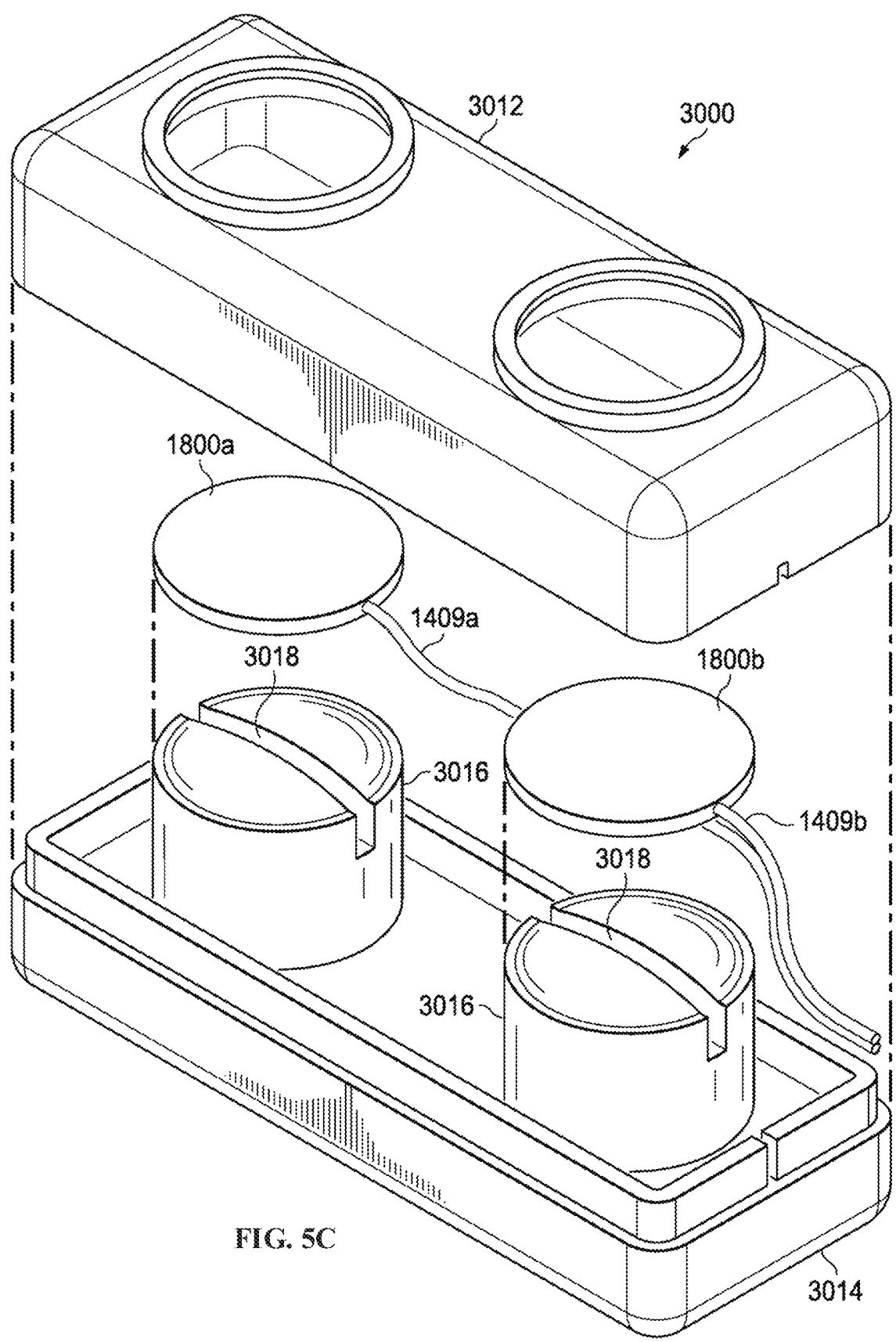
FIG. 5C is an exploded perspective view of an embodiment of the bar electrode as similarly shown in FIGS. 3 and 4.
Figure 6:
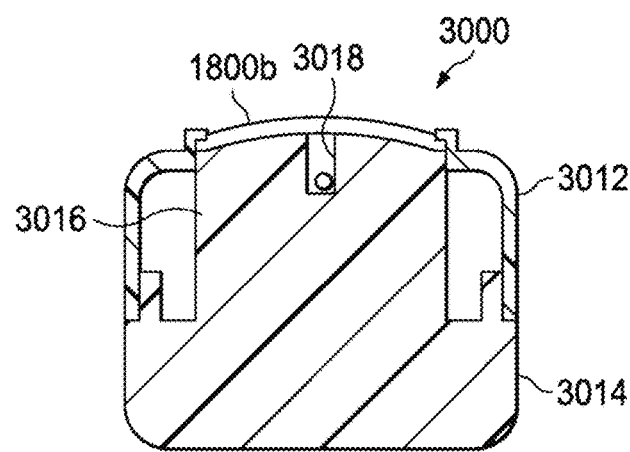
FIG. 6 is a cross-sectional side view an embodiment of the bar electrode taken along line 6-6 of FIG. 3.

Referring now to FIGS. 3-6, there is illustrated an embodiment of a bipolar stimulator bar electrode 3000 utilizing multilayered dry elastomer electrodes described hereinabove. FIG. 3 is a top view of an embodiment of the dry elastomer electrode in a bar electrode 3000, and FIG. 4 is a side view of an embodiment of the dry elastomer electrode in the bar electrode 3000 as similarly shown in FIG. 3. FIG. 5A is a cross-sectional side view of an embodiment of the bar electrode 3000 taken along line 5-5 of FIG. 3; FIG. 5B is an exploded perspective view of an embodiment of the cross-sectional view of the bar electrode 3000 shown in FIG. 5A; and FIG. 5C is an exploded perspective view of an embodiment of the bar electrode 3000 as similarly shown in FIGS. 3 and 4. FIG. 6 is a cross-sectional side view an embodiment of the bar electrode 3000 taken along line 6-6 of FIG. 3.

Typically bar electrodes are attachable to a stimulator device or electromyographic (EMG) device (not shown) and are utilized for skin or surface stimulation of peripheral nerves. It can be configured with to perform both as a stimulation electrode and a recording electrode, to record nerve and muscle action potentials and to provide electrical stimulation.

Bar electrode 3000 includes an elongated body 3010 having a top 3012 and a bottom 3014. Two cylindrical shape posts 3016 having convex upper surfaces extend up from bottom 3014. Each of posts 3016 have a slot 3018 extending there-across. An electrode, such as described herein above, 1800a and 1800b are placed across the top surfaces of posts 3016 and are positioned between top 3012 and bottom 3014. Electrodes 1800a and 1800b conform to the convex shape of the top surfaces of posts 3016. Holes in top 3012 that are positioned in alignment of posts 3016 in top 3012 permit at least a portion of the electrodes 1800a and 1800b to extend above top 3012 (see FIGS. 4 and 5).

The slots 3018 of each of the posts 3016 are configured in shape to receive the leads 1409a and 1409b of electrodes 1800a and 1800b, respectively. This facilitates the leads 1409 to extend from the bar electrode and ultimately be connected to the stimulator device (not shown).

Figure 7:
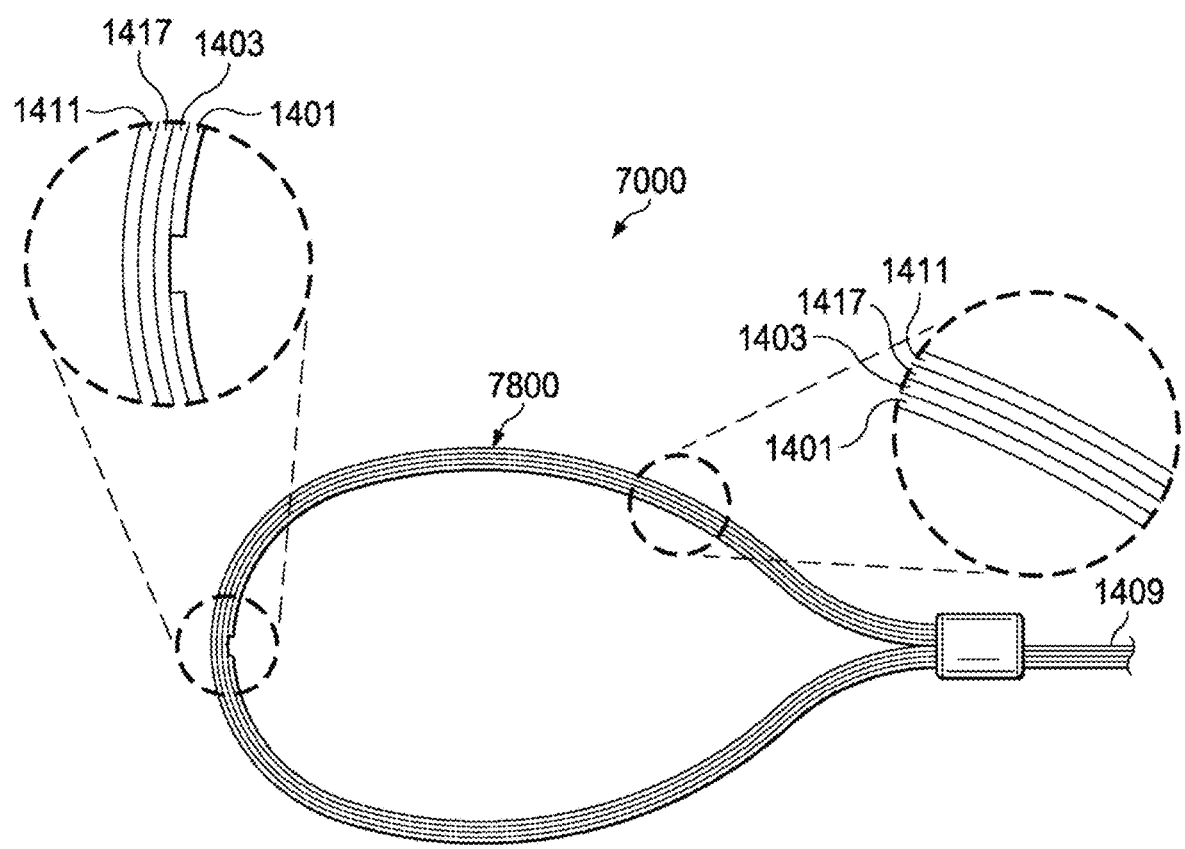
FIG. 7 is a top view of an embodiment of a digital ring electrode with portions enlarged.
Figure 8A:
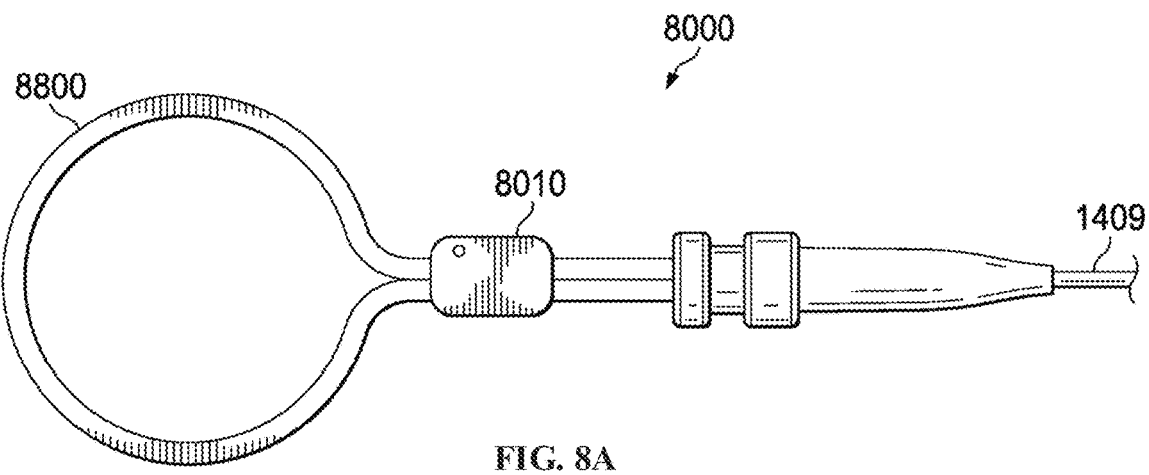
FIG. 8A is a top view of an another embodiment of a digital ring electrode with a clip.
Figure 8B:
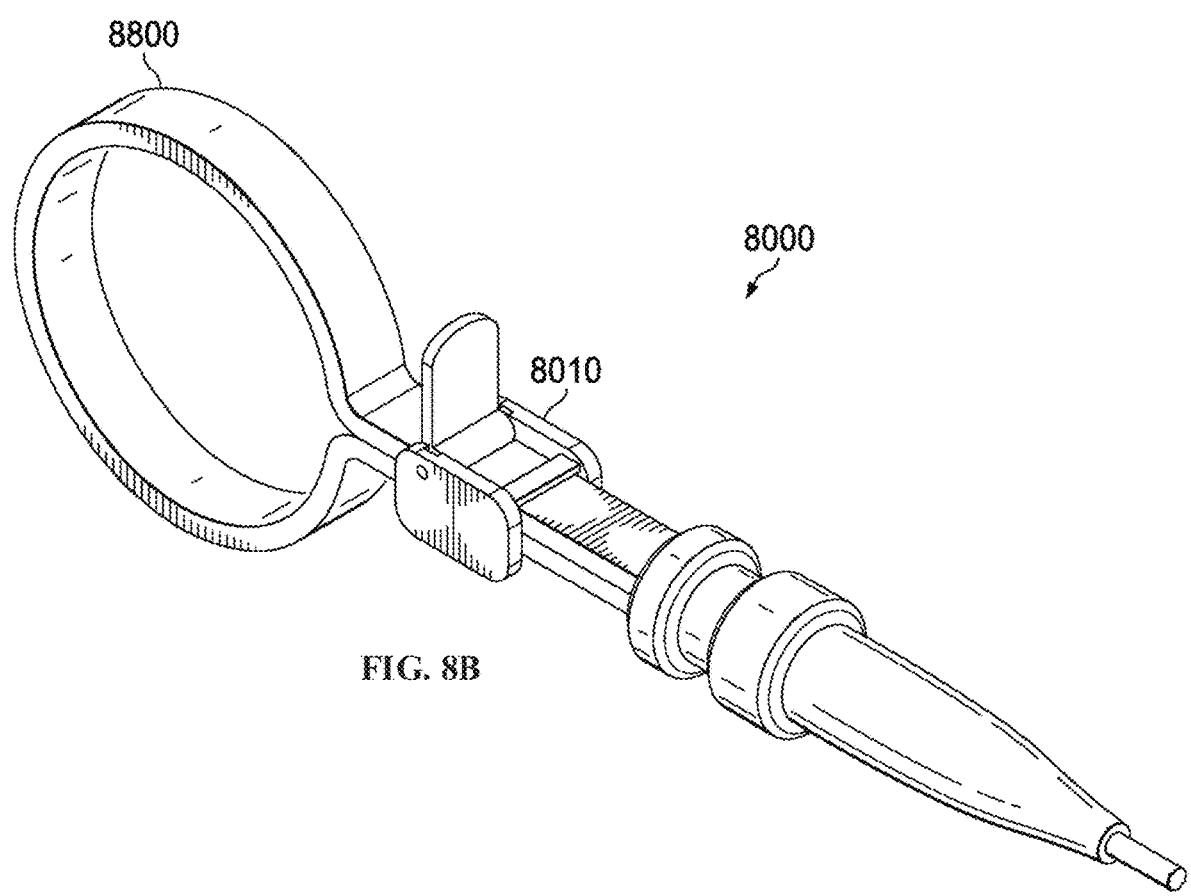
FIG. 8B is a perspective view of an embodiment of the digital ring electrode with the clip in an open position.
Figure 8C:
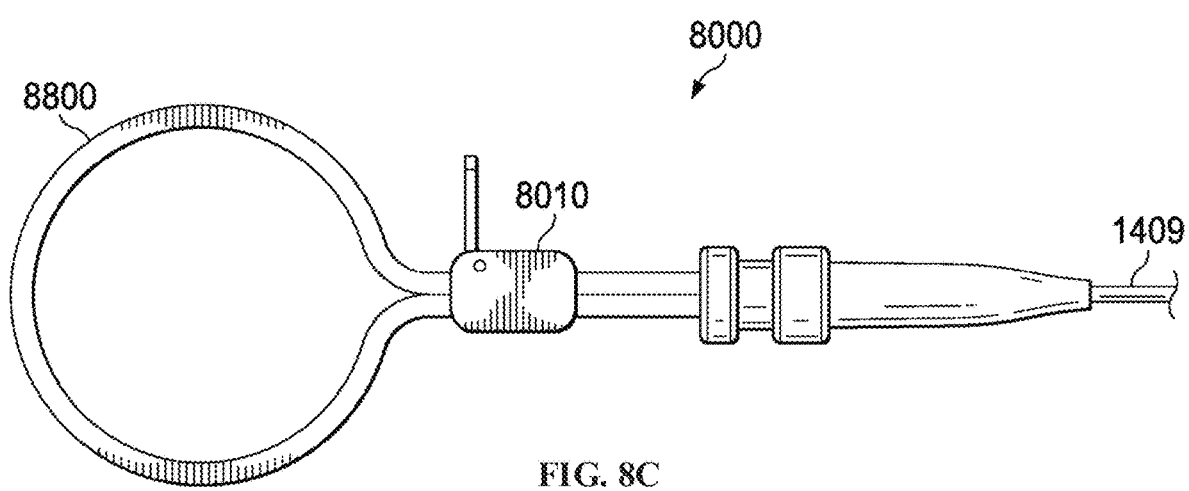
FIG. 8C is a top view of an embodiment of the digital ring electrode.
Figure 8D:
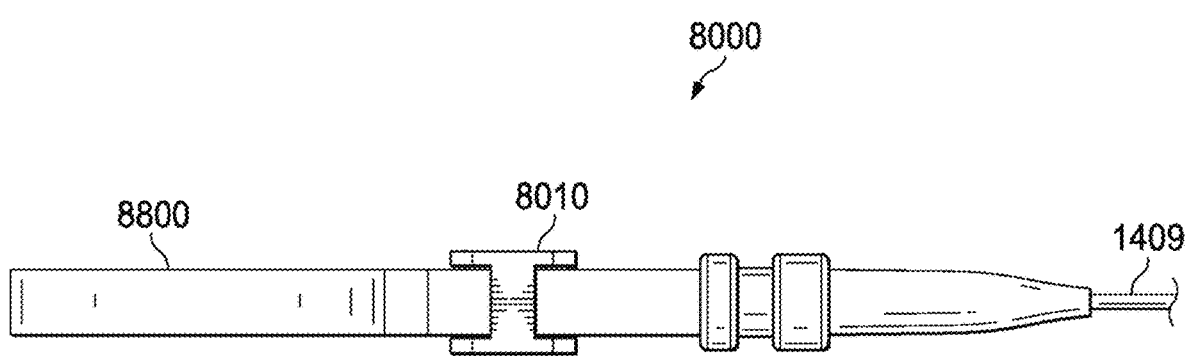
FIG. 8D is a side view of an embodiment of the digital ring electrode.

Referring now to FIGS. 7-8D, there are illustrated examples of digital ring electrodes employing multilayered dry elastomer electrodes in accordance with the principles of the claims as described herein. FIG. 7 is a top view of an embodiment of a digital ring electrode 7000 with portions enlarged. FIG. 8A is a top view of an another embodiment of a digital ring electrode 8000 with a clip; FIG. 8B is a perspective view of an embodiment of the digital ring electrode 8000 with the clip in an open position; FIG. 8C is a top view of an embodiment of the digital ring electrode 8000; and FIG. 8D is a side view of an embodiment of the digital ring electrode 8000.

It is contemplated that the embodiments of the digital ring electrodes illustrated in FIGS. 7-8D may be the same with the exception that the embodiment disclosed in FIGS. 8A-8B may employ a clip or cord lock as discussed in more detail herein below. As can be appreciated, digital ring electrodes are often used for sensory nerve stimulation or recording from the fingers and toes of patients.

Referring now to FIG. 7, there is illustrated an embodiment of noose type digital ring electrodes 7000. The ring electrode portion 7800 is a multilayered dry elastomer electrode as similarly described herein, with the inner most layer 1401 being silver filled silicone rubber. The next layer 1403 is a conductive adhesive layer, while the third layer 1417 is an Ag/AgCl film, while the outer layer 1411 is a dielectric backing layer. Layer 1401 has a gap or plurality of gaps preventing delaminating while adjusting either the radius or diameter to the given size.

Referring now to FIGS. 8A, 8B, 8C and 8D, there is illustrated another embodiment of another digital ring electrode 8000. The ring electrode portion 8800 is a multilayered dry elastomer electrode as described in the various electrode embodiments herein. Digital ring electrode 8000 includes a clip 8010 (or cord lock—not shown) which facilitates the adjustment of the size of the electrode portion 8800. When in the clip 8010 (or cord lock—not shown) is in the open position (FIG. 8B and 8C), the inner diameter of the electrode 8800 can be adjusted to facilitate the placement of the electrode 8800 onto a finger or toe of a patient and then adjusted to the proper size to secure the electrode 8800 in place. When clip 8010 (or cord lock—not shown) is in the closed position (FIG. 8), the size of the inner diameter of the electrode 8800 cannot be adjusted, thereby keeping the electrode 8800 in place the testing of the patient.

Figure 9:
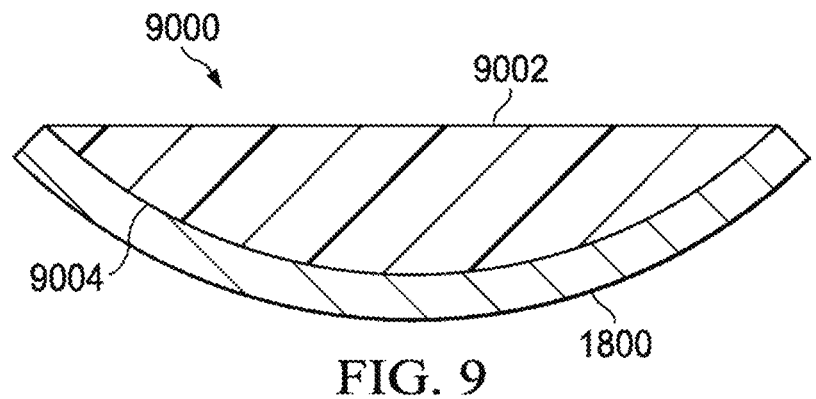
FIG. 9 is a partial cross-sectional view of an embodiment of an electrode with a disc as a backing layer wherein the electrode conforms to the convex shape of the disc.
Figure 10:
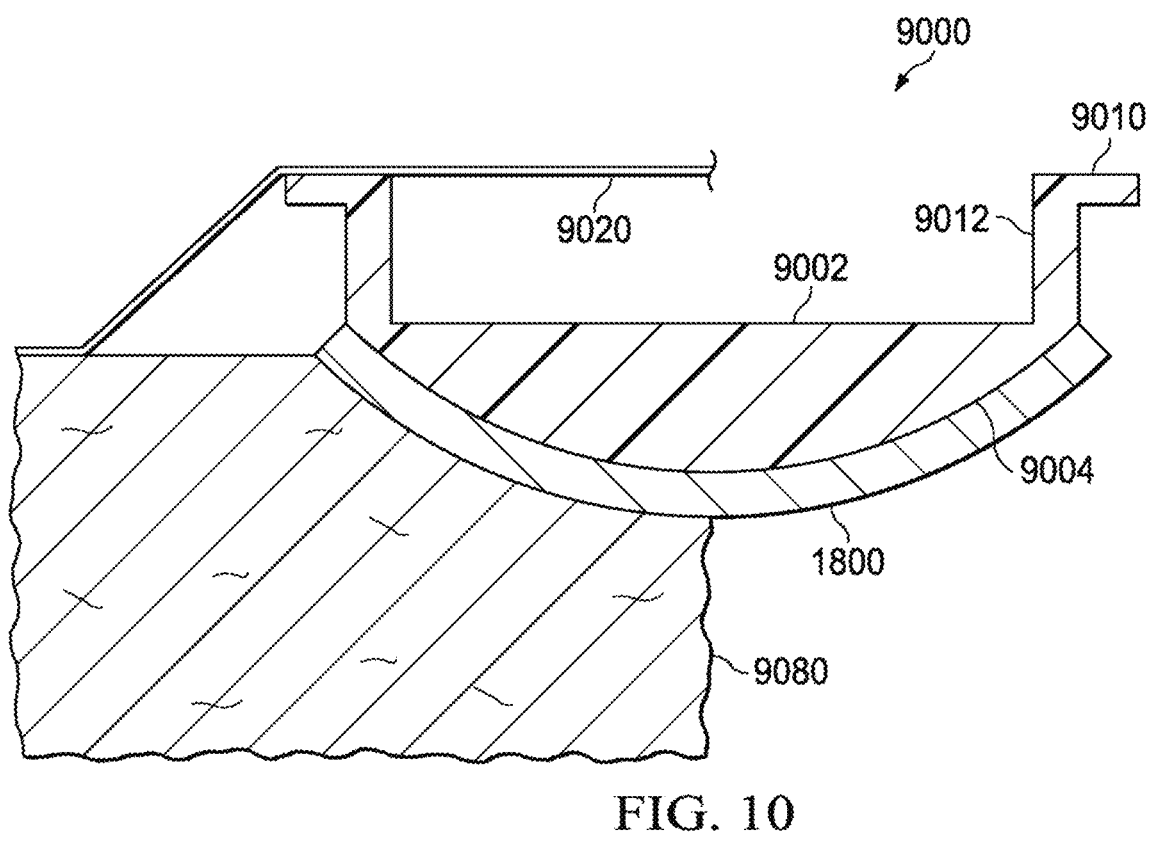
FIG. 10 is a partial cross-sectional view of an embodiment of an electrode with a disc as a backing layer where the electrode conforms to the convex shape of the disc providing uniform contact with the skin.

Referring now to FIG. 9 and FIG. 10, there is illustrated an embodiment of disc electrode 9000 employing multilayered electrodes in accordance with the principles as described herein, such as, but not limited to electrode 1400, 1600, and 1800. FIG. 9 is a partial cross-sectional view of an embodiment of the electrode 9000 with a disc as a backing layer wherein the electrode conforms to the convex shape of the disc. FIG. 10 is a partial cross-sectional view of an embodiment of the electrode 9000 with a disc as a backing layer where the electrode conforms to the convex shape of the disc providing uniform contact with the skin.

As illustrated, the disc electrode 9000 includes a disc 9002 having a convex outer surface 9004, a cylindrical wall 9012 and a flange 9010. An electrode 1800 is attached to the convex surface 9004 of disc 9002 for placement providing uniform contact against the patient's skin 9080. An adhesive 9020 can be utilized to secure the disc electrode 9000 to the patient during use.

Figure 15:
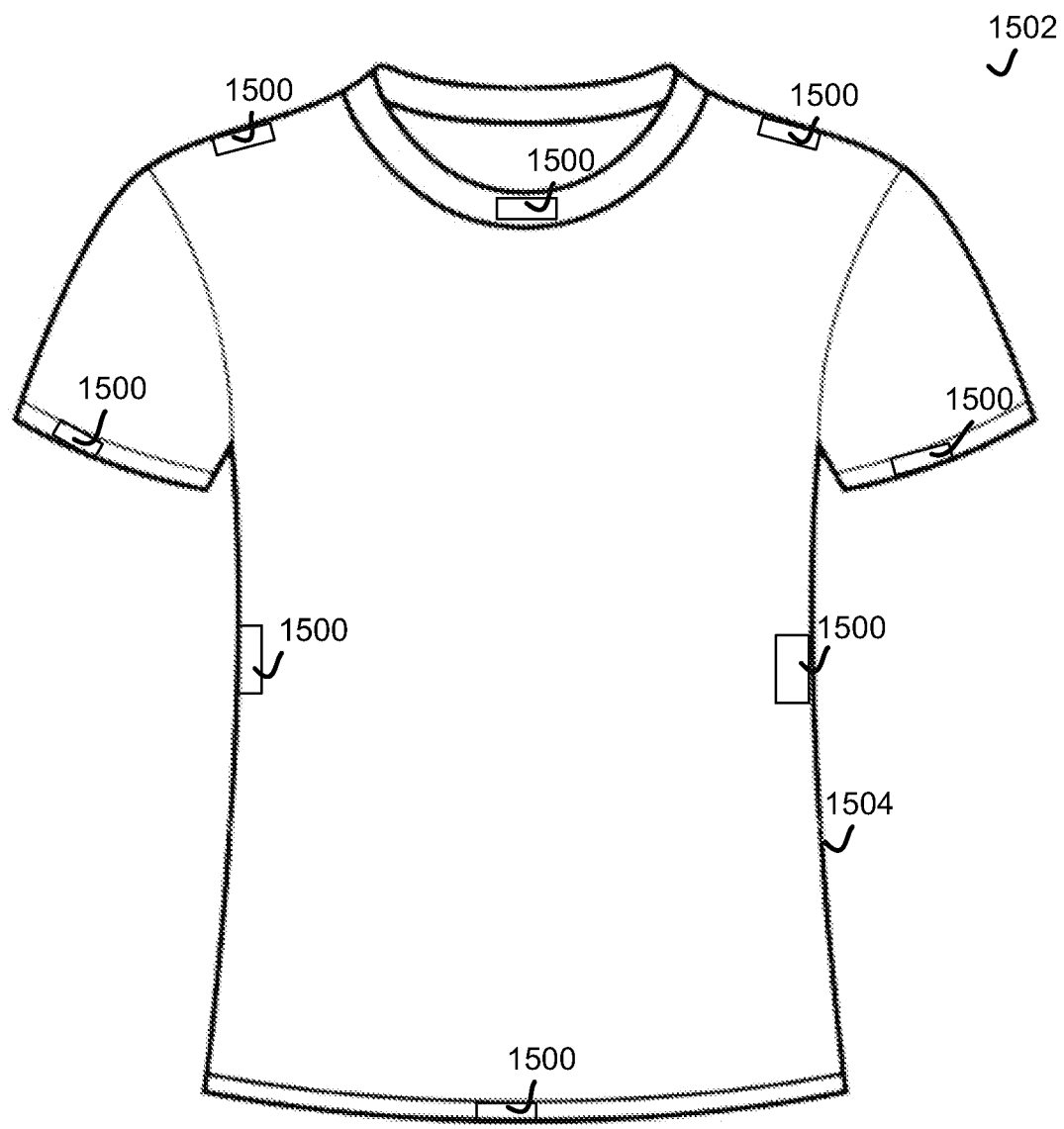
FIG. 15 illustrates a schematic diagram of an embodiment of an electrode in a wearable garment.

FIG. 15 illustrates a schematic diagram of an embodiment of the electrode 1500 in a wearable garment 1502. The electrode 1500 may include any of the embodiments of electrodes described herein. In this embodiment, the electrode 1500 is incorporated in seams, hems, necklines, or pockets of a shirt 1502. For example, the electrode 1500 may be sewn into the stitch seams 1504 of the garment 1502, such as stitched in the seam. The electrode 1500 may also be glued to the fabric of the garment. In another example, a laminate layer of the electrode 1500 may secure the electrode to the fabric or textile of the garment 1502. The textile of the wearable garment 1502 in an embodiment is a compression fabric that stretches and compresses against the skin tissue. Though a shirt is illustrated herein, the wearable garment 1502 may include pants, underwear, bras, hats, belts, socks, gloves or other types of garments. In addition, though eight electrodes 1500 are illustrated, the garment 1502 may include a single electrode 1500 or two or more electrodes 1500.

The interfacing or upper layer of the electrode 1500 includes the metal integral conductive silicone rubber (or elastomer) which, by way of example and not limitation, may be a gold, silver, silver plated copper, or other conductive metal plated material filled silicone or a metal plated material filled silicone. For example, the material may also be described as a silicone rubber with metal fillers, or a conductive filler material dispersed substantially throughout the polymer, plastic, or rubber material. The conductive filler material may include a powder or fine particulate material. Other upper layers may also include an elastomer covering, e.g. a cover film to protect the elastomer from exposure and/or a water-resistant layer.

In one embodiment, the one or more incorporated electrodes 1500 are configured for continuous or periodic physiological monitoring, such as heart rate, respiration rate, electrocardiogram, fetus monitoring, etc. The electrodes 1500 may communicate via a wireless connection with a remote device, such as a smart watch, smart phone, computer, or other device. In another embodiment, the one or more incorporated electrodes 1500 are configured to provide an electro-stimulation to the wearer of the garment 1502 for therapeutic purposes. The wearer of the garment 1502 may include a person, pet, livestock, or other animal.

Figure 16:
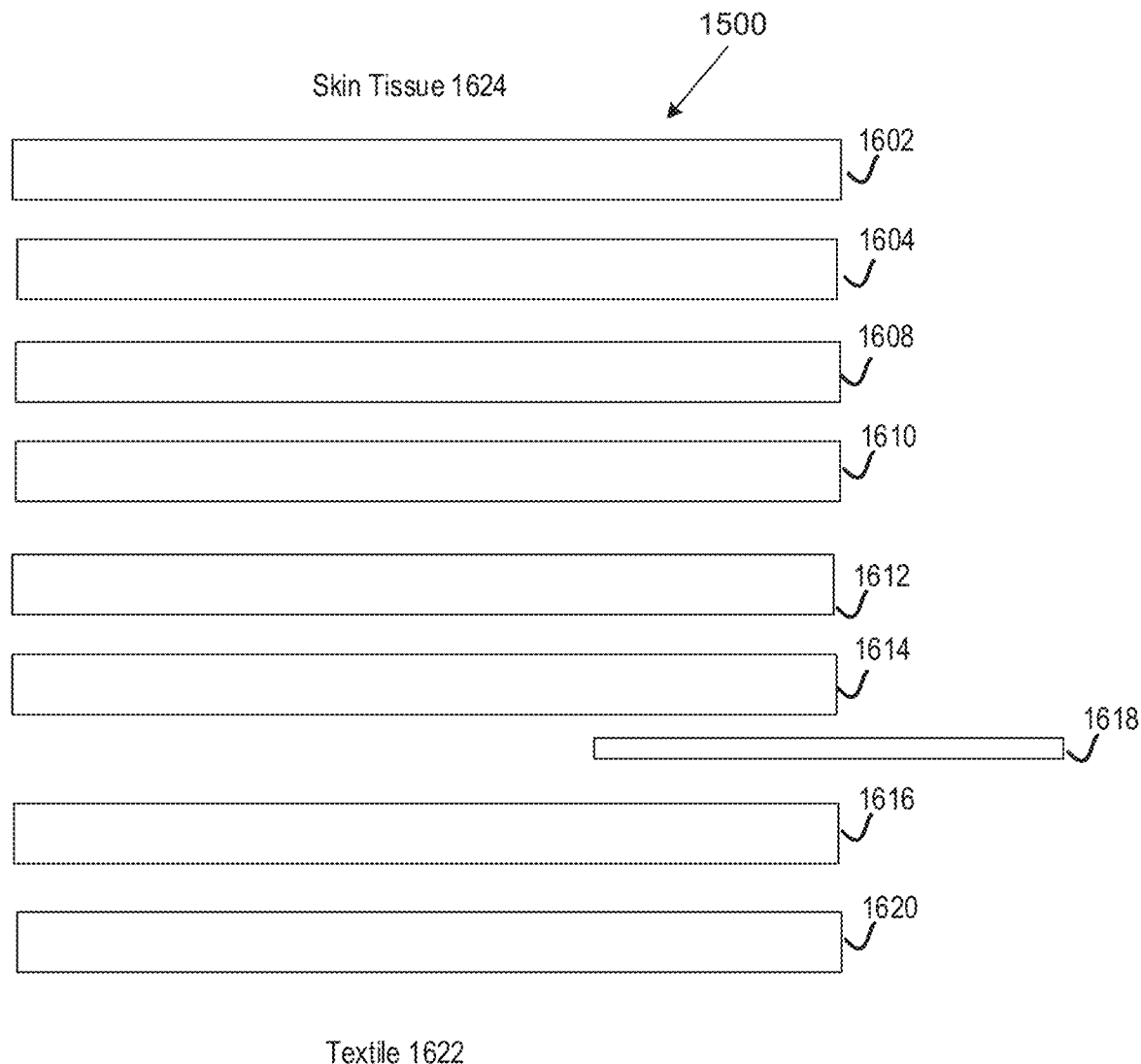
FIG. 16 illustrates a schematic block diagram of an embodiment of the electrode that may be incorporated within the wearable garment.

FIG. 16 illustrates a schematic block diagram of an embodiment of the electrode 1500 that may be incorporated within the garment 1502. The first layer 1602 is configured to lay adjacent to skin tissue 1624 of a wearer of the garment 1502 and includes a cover film to protect the electrode 1500 from exposure. A second layer 1604 includes a water-resistant material to protect the electrode 1500 from sweat and other moisture. The water-resistant material and the cover film preferably cover at least a portion of the surface of the electrode 1500 that is exposed to the wearer. A third layer 1608 includes the metal integral conductive silicone rubber (or elastomer) which, by way of example and not limitation, may be a gold, silver, silver plated copper, or other conductive metal plated material filled silicone. The silicone includes a silicon-containing synthetic polymer silicone or other material including silicone, such as silicone elastomers, silicone rubber, etc.

The electrode 1500 further includes a fourth layer 1610 which may be a conductive adhesive gel layer to adhere to the third layer 1608. A fifth layer 1612 includes a conductive carbon film to adhere to the conductive adhesive gel layer in the fourth layer 1610. A sixth layer 1614 includes a conductive metal sheet, wherein the metal may be silver or other appropriate conducting metal or alloy. The seventh layer 1616 includes a dielectric/non-conducting flexible backing sheet. An electrical lead 1618 may be positioned and secured between the sixth layer 1614 and the seventh layer 1616. The lead 1618 and the conductive metal layer 1614 may be coupled in a same layer, e.g., such as a layer of silver coupled to a silver lead. An adhesive or laminate layer 1620 may be incorporated into the seventh layer 1616 or as an additional layer to attach the electrode 1500 to the textile 1622 of the garment 1502.

In one or more embodiments, the lead 1618 may include a conductive ink that is sewn into the textile as a thread, glued on or printed onto the textile 1622. Alternatively or in addition, the lead 1618 may include a conductive metal that is sewn into the hems and/or seams of the garment 1502 or glued onto the textile 1622. In one embodiment, the electrical lead 1618 facilitates the delivery of energy to the electrode 1500 from a power source (not shown) for electrical stimulation. In another embodiment, the electrical lead 1618 may conduct detected electric physiological signals of the body for heart monitoring, respiration monitoring, electrocardiograms, fetus monitoring or other types of monitoring.

One or more of the above layers in the electrode 1500 may be absent in different embodiments herein. For example, the first layer 1602 and the second layer 1604 may be combined into a single cover film that is water-resistant. In another example, the first layer 1602 and the second layer 1604 may not be present, and the third layer 1608 with the metal integral conductive silicone rubber (or elastomer) may be configured to lay adjacent to the skin tissue 1624 of a wearer of the garment.

In another embodiment, the electrode 1500 may only include the third layer 1608 with the metal integral conductive silicone rubber (or elastomer) configured to lay adjacent to the skin tissue 1624 of a wearer of the garment and the sixth layer 1614 of a conductive metal sheet. The adhesive or laminate layer 1620 may be incorporated to attach the electrode 1500 to the textile 1622 of the garment and provide a non-conducting layer. The lead 1618 may be included as a conductive ink or metal attached to the sixth layer 1614. The leads 1618 may be sewn into the seams of the garment or incorporated in the textile 1622 of the garment.

Figure 17:
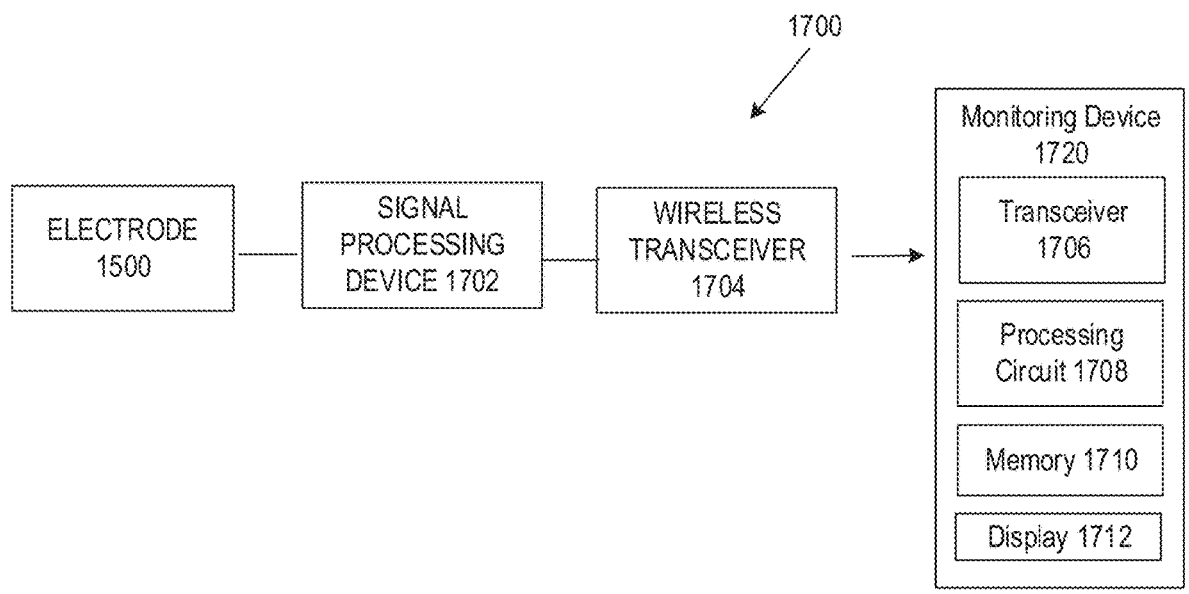
FIG. 17 illustrates a schematic block diagram of an embodiment of a device for physiological monitoring using one or more electrodes incorporated into the wearable garment.

FIG. 17 illustrates a schematic block diagram of an embodiment of a device 1700 for physiological monitoring using one or more electrodes 1500 incorporated into a garment 1502. The one or more electrodes 1500 may be stitched into the garment or attached through an adhesive or laminate layer 1620. The device 1700 further includes a signal processing device 1702 that receives the analog electrical signals detected by the electrode 1500. The signal processing device 1702 amplifies, filters and converts the analog electrical signals into digital signals. The signal processing device 1702 may then provide the digital signals to the wireless transceiver 1704 for transmission to a monitoring device 1720, such as a smart watch, smart phone, computer or other processing device.

The wireless transceiver 1704 may implement a short range communication protocol. For example, the wireless transceiver 1704 may include an IEEE 802.11ah, Zigbee, IEEE 802.15-11 or WLAN (such as an IEEE 802.11 standard protocol) compliant transceiver. In another example, the wireless transceiver 1704 may include a short range transceiver that may operate using RFID, short range radio frequency, Bluetooth, infrared link, or other short range wireless communication protocol. In another aspect, the wireless transceiver may also include an interface for communicating over a cellular network. Each electrode 1500 may include a signal processing device 1702 and wireless transceiver 1702 or a plurality of electrodes may be coupled to the same signal processing device 1702 and wireless transceiver 1702 through one or more leads 1618. The leads 1618 may be conductive metal sewn into the seams of the garment or incorporated in the garment as conductive ink or threads.

The monitoring device 1720 includes a transceiver 1706 for communicating with the wireless transceiver 1706 using a short range wireless communication. For example, the wireless transceiver 1706 may include IEEE 802.11ah, Zigbee, IEEE 802.15-11 or WLAN (such as an IEEE 802.11 standard protocol) compliant transceiver. The transceiver may include a short range transceiver that may operate using RFID, short range radio frequency, Bluetooth, infrared link, or other short range wireless communication protocol. In another aspect, the wireless transceiver may also include an interface for communicating over a cellular network. The transceiver 220 may be also configured to communicate with one or more other devices over a LAN, MAN and/or WAN. In one aspect, the transceiver 220 may also include a wired transceiver interface, e.g., a USB port or other type of wired connection, for communication with one or more other devices over a LAN, MAN and/or WAN.

The monitoring device 1720 further includes a processing circuit 1708, memory 1710 and display 1712. The processing circuit 1708 performs one or more of the functions described herein in response to instructions stored in the memory 1710. The monitoring device 1720 includes a physiological monitoring system that can interpret the physiological signals from the electrode 1500 to determine heart rate, respiration rate, electrocardiogram, etc. The data is stored in the memory 1710 and can be uploaded into a medical record management tool and/or displayed on the display 1712.

Figure 18:
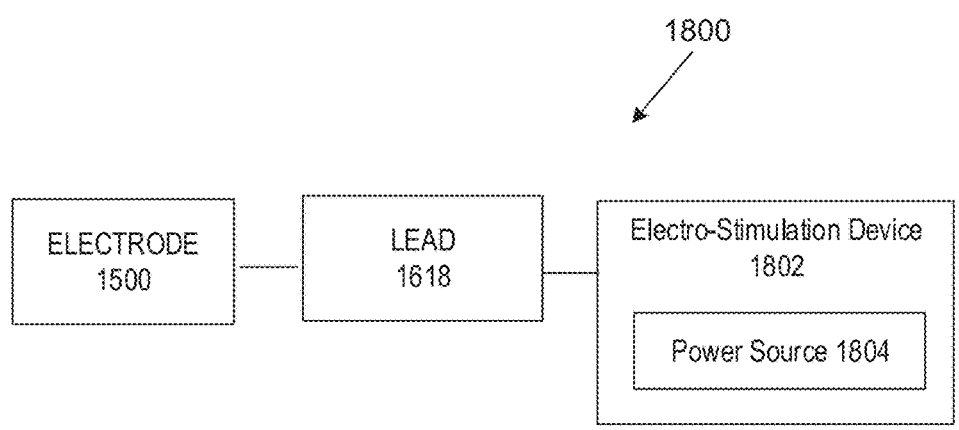
FIG. 18 illustrates a schematic block diagram of an embodiment of a device for therapeutic electro-stimulation using one or more electrodes incorporated into the wearable garment.

FIG. 18 illustrates a schematic block diagram of an embodiment of another device 1800 for therapeutic electro-stimulation. One or more electrodes 1500 are incorporated into a garment 1502 and coupled to an electro-stimulation device 1802 by one or more leads 1618. The electro-stimulation device 1802 includes a power source 1804 for generating a stimulation signal or current through the leads 1618 to the one or more electrodes 1500.

Figure 19:
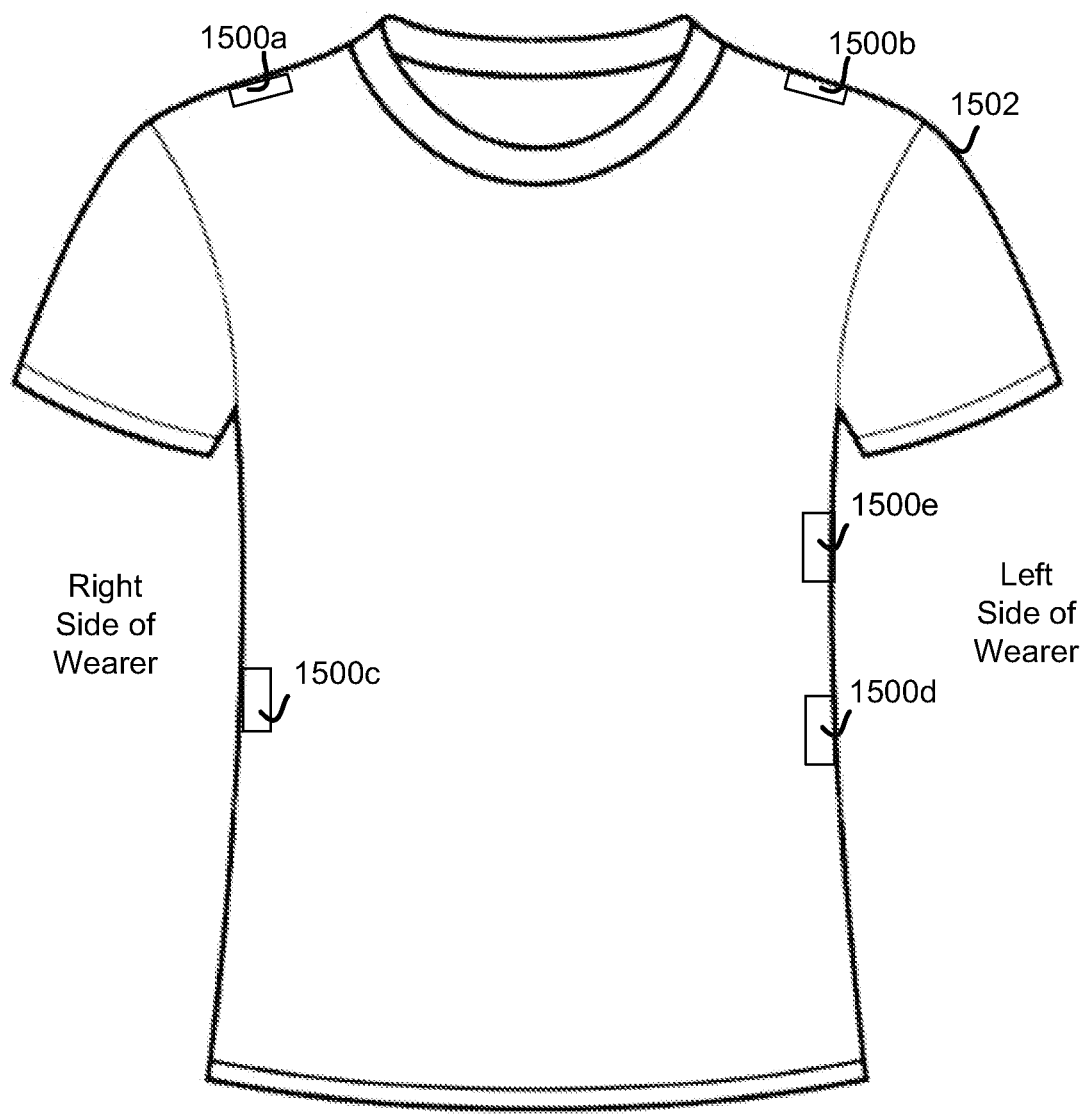
FIG. 19 illustrates a schematic block diagram of an embodiment of a garment with a plurality of electrodes for obtaining an electrocardiogram (ECG).

FIG. 19 illustrates a schematic block diagram of an embodiment of a garment 1502 with a plurality of electrodes 1500 for obtaining an electrocardiogram (ECG). In this embodiment, the electrodes 1500 are positioned in a 5 lead electrode configuration for obtaining the ECG. This configuration includes four limb electrodes—right arm (RA) 1500*a*, left arm (LA) 1500*b*, right leg (RL) 1500*c*, left leg (LL) 1500*d* and a precordial electrode 1500*e* that is positioned to monitor a lateral aspect of the left ventricle. The limb electrodes 1500*a-d* are positioned on the garment 1502 in proximity to a junction of the limb on the torso. This configuration has an advantage when the electrodes 1500 are sewn into the seams of the garment 1502. For example, RA electrode 1500*a* may be positioned at approximately the right shoulder seam of the garment 1502, LA electrode 1500*b* may be located at approximately the left shoulder seam, RL electrode 1500*c* may be located at approximately the right seam of the garment 1502 and the LL electrode 1500*d* may be located at approximately the left seam of the garment 1502. The precordial electrode 1500*e* is located at approximately the left seam of the garment 1502 in a position closer to the left arm than the LL electrode 1500*d*.

Other possible electrode configurations for ECGs may be implemented by the plurality of electrodes 1500. For example, in another 5 electrode configuration, the precordial electrode 1500*e* is positioned on the garment 1502 for proximity to the right of the sternal border at the 4th intercostal space (ICS) of the wearer. Other ECG electrode configurations may be implemented such as 3 electrode and 10-12 electrode configurations.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects of the invention have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

In one or more aspects herein, a processing circuit includes at least one processor, such as a microprocessor, micro-controller, digital signal processor, microcomputer, neural network, machine learning or Artificial Intelligence (AI) processor, Quantum processor, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing circuit further includes a memory device. The memory device is a non-transitory memory and may be an internal memory or an external memory, and the memory may be a single memory device or a plurality of memory devices. The memory may be a read-only memory, random access memory, volatile memory, non-volatile memory, static memory, dynamic memory, flash memory, cache memory, and/or any non-transitory memory device that stores digital information. The processing device performs one or more of the functions described herein in response to instructions stored in a memory device.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

The specification has described, at least in part, one or more embodiments. The one or more embodiments described are used herein, an aspect thereof, a feature thereof, a concept thereof, and/or an example thereof. A physical embodiment of an apparatus, an article of manufacture, a machine, and/or of a process that embodies the aspects described herein may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones. While particular combinations of various functions and features have been expressly described herein, other combinations of these features and functions are likewise possible. The claims are not limited by the particular examples disclosed herein and expressly incorporates these other combinations.

The invention claimed is:

1. A wearable garment, comprising:
a compression fabric; and
a plurality of electrodes coupled to the compression fabric, wherein at least one of the plurality of electrodes includes:
a first layer comprising a metal integral conductive silicone rubber material, wherein the metal integral conductive silicone rubber material is configured for positioning most proximate to a wearer of the wearable garment;
a second layer including a conducting metal sheet;
a conductive lead coupled to the second layer; and
a non-conducting layer configured to lay proximate to the compression fabric.

2. The wearable garment of claim 1, wherein each of the plurality of electrodes includes the first layer comprising the metal integral conductive silicone rubber material configured for positioning most proximate to the wearer of the wearable garment.

3. The wearable garment of claim 1, wherein the at least one of the plurality of electrodes further comprises a cover film, wherein the cover film is configured to protect the at least one of the plurality of electrodes from exposure, wherein the cover film at least includes a water-resistant material layer, wherein the water-resistant material layer is configured to protect the at least one of the plurality of electrodes from exposure to at least moisture.

4. The wearable garment of claim 1, wherein the conductive lead is configured for connection to an electro-stimulation device for conducting an electrical stimulation signal to the at least one of the plurality of electrodes.

5. The wearable garment of claim 1, wherein the conductive lead is configured for connection to a wireless transceiver for transmission of physiological signals detected by the at least one of the plurality of electrodes to a monitoring device.

6. The wearable garment of claim 1, wherein the at least one of the plurality of electrodes is sewn into a stitch seam of the wearable garment.

7. The wearable garment of claim 1, wherein the non-conducting layer includes an adhesive configured to lay proximate to the compression fabric and adhere the at least one of the plurality of electrodes to the compression fabric of the wearable garment.

8. A device, comprising:
a wearable garment including compression fabric;
at least one electrode coupled to the compression fabric, wherein the at least one electrode includes:
a first layer comprising a metal integral conductive silicone rubber material, wherein the at least one electrode is coupled to the compression fabric to position the first layer as the most proximate layer of the at least one electrode to a wearer of the wearable garment;
a second layer including a conducting metal sheet;
a conductive lead coupled to the second layer; and
a non-conducting layer configured to lay proximate to the compression fabric; and
a wireless transceiver coupled to the at least one electrode.

9. The device of claim 8, wherein the conductive lead is configured for connection to the wireless transceiver for transmission of physiological signals detected by the at least one electrode.

10. The device of claim 8, wherein the at least one electrode is sewn into a stitch seam of the wearable garment.

11. The device of claim 8, wherein the at least one electrode is coupled to the compression fabric to position the non-conducting layer to lay most proximate to the compression fabric.

12. A wearable garment including compression fabric, comprising:
a plurality of electrodes coupled to the compression fabric of the wearable garment, wherein each of the plurality of electrodes includes:

a first electrode layer comprising a metal integral conductive silicone rubber material, wherein the first layer is positioned on an interior of the garment to lay most proximate than other electrode layers to a wearer of the wearable garment;

a second electrode layer comprising a non-conducting layer, wherein the second electrode layer is configured to lay most proximate than other electrode layers to the compression fabric of the wearable garment; and a conductive lead positioned between the first electrode layer and the second electrode layer.

13. The wearable garment of claim 12, wherein each of the plurality of electrodes further comprises:

a cover film including at least a water-resistant material, wherein the water-resistant material is configured to protect from moisture.

14. The wearable garment of claim 12, wherein the conductive lead is configured for connection to an electro-stimulation device for conducting an electrical stimulation signal to each of the plurality of electrodes.

15. The wearable garment of claim 12, wherein the conductive lead is configured for connection to a wireless transceiver for transmission of physiological signals detected by each of the plurality of electrodes to a monitoring device.

16. The wearable garment of claim 12, wherein each of the plurality of electrodes further comprises an adhesive layer proximate to the wearable garment, wherein the adhesive layer of each of the plurality of electrodes couples the plurality of electrodes to the compression fabric of the wearable garment.

17. The wearable garment of claim 12, wherein each of the plurality of electrodes is sewn into at least one of a plurality of stitch seams of the wearable garment.

* * * * *